US012303182B2

(12) United States Patent
Neal, II

(10) Patent No.: US 12,303,182 B2
(45) Date of Patent: May 20, 2025

(54) TECHNIQUES FOR IRREVERSIBLE ELECTROPORATION USING A SINGLE-POLE TINE-STYLE INTERNAL DEVICE COMMUNICATING WITH AN EXTERNAL SURFACE ELECTRODE

(71) Applicant: AngioDynamics, Inc., Latham, NY (US)

(72) Inventor: Robert E. Neal, II, Blacksburg, VA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 18/340,610

(22) Filed: Jun. 23, 2023

(65) Prior Publication Data
US 2024/0016535 A1 Jan. 18, 2024

Related U.S. Application Data

(63) Continuation of application No. 17/147,131, filed on Jan. 12, 2021, now Pat. No. 11,723,710, which is a
(Continued)

(51) Int. Cl.
*A61B 18/12* (2006.01)
*A61B 18/14* (2006.01)
(Continued)

(52) U.S. Cl.
CPC .......... *A61B 18/12* (2013.01); *A61B 18/1477* (2013.01); *A61N 1/0412* (2013.01);
(Continued)

(58) Field of Classification Search
CPC ..... A61B 18/12; A61B 18/1477; A61B 18/16; A61B 18/08; A61B 18/082; A61B 18/14;
(Continued)

(56) References Cited

U.S. PATENT DOCUMENTS 5,749,914 A 5/1998 Janssen
5,759,158 A 6/1998 Swanson
(Continued)

FOREIGN PATENT DOCUMENTS

DE 833111 3/1952
EP 0528891 B1 7/2000
(Continued)

OTHER PUBLICATIONS

Alberts et al., "Molecular Biology of the Cell," 3rd edition, Garland Science, New York, 1994, 1 page.
(Continued)

*Primary Examiner* — Thomas A Giuliani
(74) *Attorney, Agent, or Firm* — Kevin Radigan, Esq.; Heslin Rothenberg Farley & Mesiti P.C.

(57) ABSTRACT

Techniques for High-Frequency Irreversible Electroporation (HFIRE) using a single-pole tine-style internal device communicating with an external surface electrode are described. In an embodiment, a system for ablating tissue cells in a treatment region of a patient's body by irreversible electroporation without thermally damaging the tissue cells is described. The system includes at least one single-pole electrode probe for insertion into the treatment region, the single-pole electrode probe including one or more tines. The system further includes at least one external surface electrode for placement outside the patient's body and configured to complete a circuit with the single-pole electrode probe. The system also includes a control device for controlling HFIRE pulses to the single-pole tine-style electrode and the skin-surface electrode for the delivery of electric energy to the treatment region. Other embodiments are described and claimed.

20 Claims, 13 Drawing Sheets

Related U.S. Application Data continuation of application No. 15/685,355, filed on Aug. 24, 2017, now Pat. No. 10,905,492.

(60) Provisional application No. 62/423,256, filed on Nov. 17, 2016.

(51) Int. Cl.
*A61N 1/04* (2006.01)
*A61B 18/00* (2006.01)
*A61N 1/32* (2006.01)

(52) U.S. Cl.
CPC ............ *A61B 2018/00452* (2013.01); *A61B 2018/00577* (2013.01); *A61B 2018/00613* (2013.01); *A61B 2018/00791* (2013.01); *A61B 2018/00875* (2013.01); *A61B 2018/00964* (2013.01); *A61B 2018/143* (2013.01); *A61B 2018/1432* (2013.01); *A61B 2018/1475* (2013.01); *A61N 1/327* (2013.01)

(58) Field of Classification Search
CPC ............ A61B 18/1402; A61B 18/148; A61B 18/1482; A61B 2018/1425; A61B 2018/1427; A61B 2018/167; A61B 2018/00452; A61B 2018/00577; A61B 2018/00613; A61B 2018/00791; A61B 2018/00875; A61B 2018/143; A61B 2018/1432; A61B 2018/1475; A61B 2018/0016; A61B 2018/00214; A61B 2018/124; A61B 2018/1253; A61B 2018/00583; A61N 1/0412; A61N 1/327
USPC ............... 606/32–34, 41, 42; 607/115, 116; 604/20

See application file for complete search history.

(56) References Cited

U.S. PATENT DOCUMENTS

| | | | |
|---|---|---|---|
| 6,009,647 A | 1/2000 | Feingold | |
| 6,010,616 A | 1/2000 | Lewis | |
| 6,033,402 A | 3/2000 | Tu | |
| 6,055,456 A | 4/2000 | Gerber | |
| 6,135,999 A | 10/2000 | Fanton | |
| 7,871,406 B2 | 1/2011 | Nields | |
| 8,055,323 B2 | 11/2011 | Sawyer | |
| 9,700,368 B2 | 7/2017 | Callas | |
| 10,905,492 B2 * | 2/2021 | Neal, II | A61B 18/12 |
| 11,638,603 B2 | 5/2023 | Sano | |
| 11,655,466 B2 | 5/2023 | Neal, II | |
| 11,723,710 B2 * | 8/2023 | Neal, II | A61B 18/1477 606/32 |
| 11,737,810 B2 | 8/2023 | Davalos | |
| 11,890,046 B2 | 2/2024 | Neal | |
| 11,903,690 B2 | 2/2024 | Davalos | |
| 11,925,405 B2 | 3/2024 | Davalos | |
| 11,950,835 B2 | 4/2024 | O'Brien | |
| 11,952,568 B2 | 4/2024 | Neal, II | |
| 11,974,800 B2 | 5/2024 | Sano | |
| 12,059,197 B2 | 8/2024 | Davalos | |
| 2001/0043706 A1 | 11/2001 | Masuda | |
| 2004/0116935 A1 | 6/2004 | Lechot | |
| 2004/0237340 A1 | 12/2004 | Rembrandt | |
| 2005/0004567 A1 | 1/2005 | Daniel | |
| 2005/0063974 A1 | 3/2005 | Reinhard | |
| 2006/0234752 A1 | 10/2006 | Mese | |
| 2007/0016125 A1 | 1/2007 | Wong | |
| 2007/0129720 A1 | 6/2007 | Demarais | |
| 2007/0153135 A1 | 7/2007 | Han | |
| 2007/0203537 A1 | 8/2007 | Goetz | |
| 2008/0009102 A1 | 1/2008 | Yang | |
| 2008/0172104 A1 | 7/2008 | Kieval | |
| 2008/0183256 A1 | 7/2008 | Keacher | |
| 2008/0319511 A1 | 12/2008 | Pless | |
| 2009/0326346 A1 | 12/2009 | Kracker | |
| 2010/0030211 A1 * | 2/2010 | Davalos | A61N 1/327 606/41 |
| 2010/0160906 A1 | 6/2010 | Jarrard | |
| 2010/0222377 A1 | 9/2010 | Crooks | |
| 2010/0261994 A1 * | 10/2010 | Davalos | A61B 18/1477 600/407 |
| 2011/0064371 A1 | 3/2011 | Leatherman | |
| 2011/0190851 A1 | 8/2011 | Kelly | |
| 2011/0238057 A1 * | 9/2011 | Moss | A61B 18/1477 606/41 |
| 2012/0090643 A1 | 4/2012 | Bertsch | |
| 2012/0136347 A1 | 5/2012 | Brustad | |
| 2012/0220998 A1 * | 8/2012 | Long | A61B 18/1206 606/41 |
| 2012/0265183 A1 | 10/2012 | Tulleken | |
| 2013/0023871 A1 | 1/2013 | Collins | |
| 2013/0030430 A1 * | 1/2013 | Stewart | A61N 1/327 606/41 |
| 2013/0033977 A1 | 2/2013 | Lin | |
| 2013/0090346 A1 | 4/2013 | Johns | |
| 2013/0110103 A1 | 5/2013 | Assmus | |
| 2013/0296908 A1 | 11/2013 | Schulte | |
| 2013/0338761 A1 | 12/2013 | Plowiecki | |
| 2014/0276748 A1 | 9/2014 | Ku | |
| 2015/0134584 A1 | 5/2015 | Nakagawa | |
| 2016/0058493 A1 | 3/2016 | Neal, II | |
| 2016/0143398 A1 | 5/2016 | Kim | |
| 2016/0310203 A1 | 10/2016 | Gaspredes | |
| 2016/0337310 A1 | 11/2016 | Faccin | |
| 2017/0086713 A1 | 3/2017 | Pushpala | |
| 2017/0360323 A1 | 12/2017 | Li | |
| 2018/0028260 A1 | 2/2018 | Onik | |
| 2018/0036529 A1 | 2/2018 | Jaroszeski | |
| 2018/0132922 A1 | 5/2018 | Neal, II | |
| 2018/0177543 A1 | 6/2018 | You | |
| 2019/0023804 A1 | 1/2019 | Onik | |
| 2019/0254736 A1 | 8/2019 | Wham | |
| 2023/0157759 A1 | 5/2023 | Garcia | |
| 2023/0212551 A1 | 7/2023 | Neal, II | |
| 2023/0248414 A1 | 8/2023 | Sano | |
| 2023/0355293 A1 | 11/2023 | Rafael | |
| 2023/0355968 A1 | 11/2023 | Davalos | |
| 2024/0008911 A1 | 1/2024 | Davalos | |
| 2024/0074804 A1 | 3/2024 | Neal | |
| 2024/0173063 A1 | 5/2024 | Neal, II | |
| 2024/0268878 A1 | 8/2024 | Davalos | |
| 2024/0277245 A1 | 8/2024 | Davalos | |
| 2024/0299076 A1 | 9/2024 | O'Brien | |

FOREIGN PATENT DOCUMENTS

| | | |
|---|---|---|
| EP | 1061983 B1 | 11/2004 |
| EP | 0935482 B1 | 5/2005 |
| EP | 1406685 B1 | 6/2008 |
| EP | 1424970 B1 | 12/2008 |
| JP | 4252316 A | 4/2009 |
| WO | 2023172773 A1 | 9/2023 |
| WO | 2024081749 A2 | 4/2024 |

OTHER PUBLICATIONS

Bondarenko, A. and G. Ragoisha, Eis spectrum analyser (the program is available online at http://www.abc.chemistrybsu.by/vi/analyser/) (Accessed Aug. 28, 2020).

Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.

Mercadal, Borja et al. "Dynamics of Cell Death After Conventional IRE and H-Fire Treatments", Annals of Biomedical Engineering, vol. 48, No. 5, 2020, p. 1451-1462.

(56) References Cited

OTHER PUBLICATIONS

Neal II et al., "A Case Report on the Successful Treatment of a Large Soft-Tissue Sarcoma with Irreversible Electroporation," Journal of Clinical Oncology, 29, pp. 1-6, 2011.

PCT Application No. PCT/2011/062067, International Preliminary Report on Patentability dated May 28, 2013. 7 pages.

PCT Application No. PCT/2011/066239, International Preliminary Report on Patentability dated Jun. 25, 2013. 7 pages.

PCT Application No. PCT/US15/30429, International Report on Patentability dated Nov. 15, 2016. 7 pages.

PCT Application No. PCT/US19/51731 (VTIP-A1001-PCT), International Preliminary Report on Patentability dated Mar. 23, 2021, 13 pages.

PCT Application No. PCT/US2010/029243, International Search Report, 4 pgs, (Jul. 30, 2010), Written Opinion, 7 pgs, (Jul. 30, 2010), and International Preliminary Report on Patentability, 8 pgs, (Oct. 4, 2011).

Pending Application No. PCT/US21/51551 (VTIP-A1018-PCT), International Search Report and Written Opinion dated Dec. 29, 2021, 14 pages.

Pending Application No. PCT/US23/15118 (VTIP-A1023-PCT), International Search Report and Written Opinion dated Jul. 31, 2023, 18 pages.

Korohoda, W. et al. "Reversible and Irreversible Electroporation of Cell Suspensions Flowing Through a Localized DC Electric Field", Cellular & Molecular Biology Letters, vol. 18 (2013), pp. 102-119 (published Dec. 27, 2012).

Notice of Allowance dated Jun. 21, 2024 for U.S. Appl. No. 16/938,778 (pp. 1-10).

Notice of Allowance dated Jul. 24, 2024 for U.S. Appl. No. 16/938,778 (pp. 1-2).

Notice of Allowance dated Sep. 17, 2024 for U.S. Appl. No. 17/074,867 (pp. 1-8).

Pending Application No. PCT/US23/76626 (VTIP-A1024-PCT), International Search Report and Written Opinion, dated Apr. 28, 17, 2024, 12 pages.

Pending Application No. PCT/US23/76626 (VTIP-A1024-PCT), International Search Report and Written Opinion, dated Apr. 17, 2024, 12 pages.

Reti, I. M. and Davydow, D. S., "Electroconvulsive Therapy and Antibiotics: A Case Report", J. ECT, vol. 23, No. 4, Dec. 29, 2007, pp. 289-290.

\* cited by examiner

TECHNIQUES FOR IRREVERSIBLE ELECTROPORATION USING A SINGLE-POLE TINE-STYLE INTERNAL DEVICE COMMUNICATING WITH AN EXTERNAL SURFACE ELECTRODE

RELATED APPLICATIONS

This application is a continuation of U.S. patent application Ser. No. 17/147,131, filed Jan. 12, 2021, now U.S. Pat. No. 11,723,710, issued Aug. 15, 2023, which is a continuation of U.S. patent application Ser. No. 15/685,355, filed Aug. 24, 2017, now U.S. Pat. No. 10,905,492, issued Feb. 2, 2021, which claims the benefit of priority under 35 U.S.C. § 119 (e) to U.S. Provisional Application No. 62/423,256, filed Nov. 17, 2016, the content of each of which are hereby incorporated by reference in their entireties.

FIELD OF THE DISCLOSURE

The disclosure generally relates to high-frequency irreversible electroporation techniques utilizing at least one single-pole tine-style probe device in communication with at least one external surface electrode.

BACKGROUND

Irreversible electroporation (IRE) uses the delivery of a series of brief electric pulses to alter the native transmembrane potential of cell membranes, with the cumulative strength of the pulsing protocol sufficient to result in the formation of irrecoverable nano-scale defects that ultimately result in death of the cell. Pulse delivery protocols may use irreversible electroporation pulses to treat targeted tissue, sometimes of significant volume, without inducing extracellular-matrix (ECM)-destroying extents of Joule heating—i.e., the structural proteins in a volume of tissue, such as collagen, are preserved. This permits the use of irreversible electroporation for the treatment of targeted aberrant masses without damaging adjacent or internal critical structures, permitting treatment in regions contraindicated for other forms of focal targeted therapies.

A key problem with known irreversible electroporation procedures is the occurrence of muscle contractions caused by the flow of electrical current through muscle tissue. Systemic paralytics or other muscle blockades must be administered prior to the IRE treatment. For traditional IRE pulse protocols using a single needle with surface electrode, the muscle activation has proven prohibitive in experiment in vivo trials, where clinically acceptable ablation zones cannot be achieved due to the extensive muscle contractions which often cannot be reasonably attenuated with traditional muscle blockades. Muscle contractions can be reduced by using High Frequency Irreversible Electroporation (HFIRE) protocols relative to standard IRE protocols. In the invention described herein. HFIRE pulse parameters known to reduce muscle contractions, combined with the dispersion of electrical current over the increased tissue volume of the single-pole tine-style device, and also combined with an external surface electrode, are used to achieve significantly larger, more spherical ablations with reduced muscle twitching, when compared with standard IRE protocols.

Unlike Radiofrequency Ablation (RFA), which uses continuous low voltage AC-signals, the mechanism of action for IRE relies on very intense, but brief, electric fields. Thus, typical IRE protocols involve placing an anode and cathode directly within or around a targeted volume, to focus the targeted energy in the region of interest. However, proper insertion of multiple probes may be difficult, and a resulting ablation may not be of a desirable shape or size. The use of a single bipolar or unipolar probe may make placement easier, but the size of an ablation may be too small, especially when using energy levels low enough to avoid thermal damage to a region of interest. Increasing energy levels while using a single probe may increase the likelihood of electrical arcing and/or exceeding the generator pre-set ampere limits, resulting in procedural delay or failure. Another challenge when using a bipolar probe is the resulting ablation shape which is typical oblong instead of a more desirable spherical shape. Thus, improved techniques for accurate and easy placement of one or more probes, while maintaining sufficient ablation size, desired ablation shape, and energy levels that avoid thermal damage are desired.

BRIEF SUMMARY OF THE INVENTION

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

According to at least one embodiment, a method for ablating tissue cells in a treatment region of a patient's body is provided comprising inserting at least one electrode probe into the treatment region, the electrode probe including one or more deployable tines, placing at least one surface electrode on a surface of an organ of the patient, deploying the one or more deployable tines of the at least one electrode probe into the treatment region, applying electrical pulses between the electrode probe and the surface electrode in an amount sufficient to induce irreversible electroporation of the treatment region, but insufficient to induce significant muscle contractions in the patient. The organ is skin. The one or more deployable tines may be arranged in multiple tiers around a shaft of the at least one electrode probe. The step of applying electrical pulses may include applying the electrical pulses having a pulse width of between 100 nanoseconds and 10 microseconds. The electrical pulses may be delivered in burst widths of 500 nanoseconds to 1 millisecond. The time delay between the bursts may be between 1 millisecond and 5 seconds. The electrical pulses may be bi-phasic. The step of applying electrical pulses may be sufficient to create a substantially spherical ablation zone and may include applying the electrical pulses in a pattern which has been predetermined to maintain the temperature of the treatment region below 70 degrees C. The one or more tines may each include one or more sensors. During the step of applying electrical pulses, the one or more sensors may be capable of detecting the size, temperature, conductivity, shape or extent of ablation of the treatment region. The delivery of a paralytic may not be required prior to the step of applying electrical pulses.

According to another embodiment, a method for treating tissue cells in a treatment region of a patient's body is provided comprising inserting at least one electrode probe into the treatment region, the electrode probe including one or more deployable tines; placing at least four surface electrodes on the patient's skin, deploying the one or more deployable tines of the at least one electrode probe into the treatment region, applying electrical pulses between the electrode probe and the at least four surface electrodes to produce a first target treatment region sufficient to induce irreversible electroporation of the treatment region, but insufficient to induce tissue cell destruction by thermal damage, applying electrical pulses in a sequential manner between the electrode probe and the at least four surface electrodes to produce a second target treatment region that surrounds a marginal area surrounding the first target treatment region in an amount sufficient to induce irreversible electroporation of the treatment region, but insufficient to induce tissue cell destruction by thermal damage.

According to another embodiment, a method for ablating tissue cells in a treatment region of a patient's body is provided comprising inserting at least one electrode probe into the treatment region, the electrode probe including one or more deployable tines, placing at least one surface electrode on a surface of an organ of the patient, deploying the one or more deployable tines of the at least one electrode probe into the treatment region, applying electrical pulses between the electrode probe and the surface electrode in an amount sufficient to induce irreversible electroporation of the treatment region, but insufficient to induce tissue cell destruction by thermal damage. The one or more deployable tines may be arranged in multiple tiers around a shaft of the at least one electrode probe. The step of applying electrical pulses includes applying the electrical pulses having a pulse width of between 100 nanoseconds and 10 microseconds. The electrical pulses may be delivered in burst widths of 500 nanoseconds to 1 millisecond. The time delay between the bursts may be between 1 millisecond and 5 seconds. The electrical pulses are bi-phasic. The step of applying electrical pulses may include applying the electrical pulses in a pattern which has been predetermined to maintain the temperature of the treatment region below 70 degrees C.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION

Figure 1:
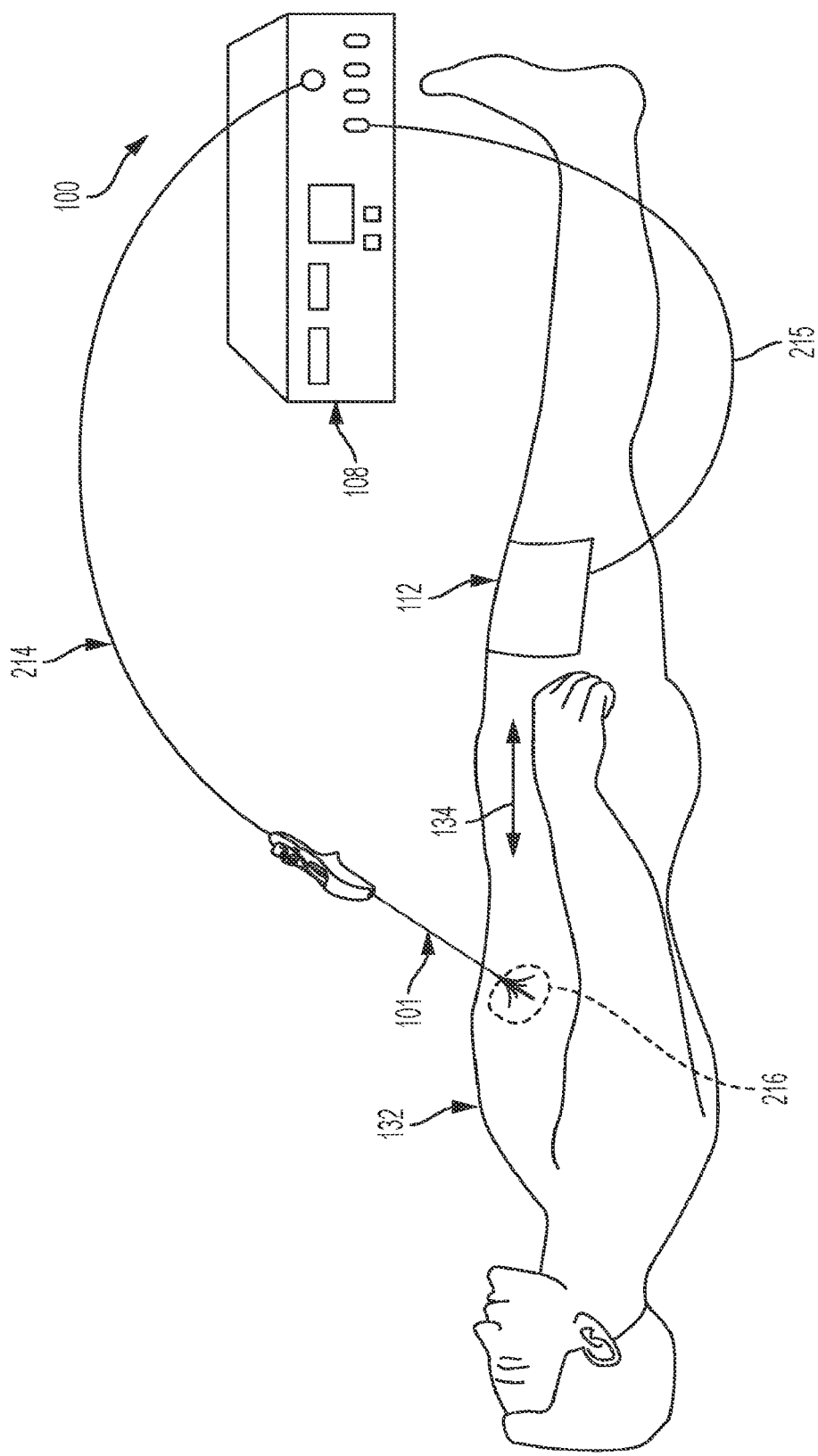
FIG. 1 illustrates a plan view of an embodiment of an HFIRE system including a tined electrode probe inserted into a target tissue of a patient.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention. As used herein, distal refers to a direction away from or distant from the point of reference, in this case the physician or user. Proximal refers to a direction toward or near to the physician or user. The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein are techniques for High Frequency Irreversible Electroporation (HFIRE) using a single-pole tine-style insertable device communicating with an external surface electrode. In an embodiment, a system for ablating tissue cells in a treatment region of a patient's body by HFIRE without thermally damaging the tissue protein structures is described. The system includes at least one single-pole electrode probe for insertion into the treatment region, the single-pole electrode probe including one or more expandable tines. The system further includes at least one surface electrode for placement on the surface of the patient's body or organ and configured to complete a circuit with the single-pole tine style electrode probe. The system also includes a control device for controlling HFIRE pulses to the single-pole electrode and the skin-surface electrode for the delivery of electric energy to the treatment region. Other embodiments are described and claimed.

These procedural descriptions and representations are used by those skilled in the art to most effectively convey the substance of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator No such capability of a human operator is necessary, or desirable in most cases, in any of the operations described herein which form part of one or more embodiments. Rather, the operations are machine operations. Useful machines for performing operations of various embodiments include general purpose digital computers, controllers, or similar devices.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

As disclosed herein, the reference to "electrodes" may include physically discrete components that serve to deliver the electric pulses, but it can also indicate individual energized surface components within a single device. Electrode devices known in the art include single pole and bipole, non-tined designs as well as tined electrode probes. As disclosed herein, a non-tined electrode device refers to a device which delivers electrical pulses including a single shaft having an energizeable surface component for the delivery of electrical energy. The non-tined electrode may be either single pole wherein the electrical current travels between the non-tined electrode and a surface electrode, or may be of a bipolar design wherein the shaft has one or more energizeable surface components wherein the electrical current travels between the surface components on the device. A tine-style electrode device refers to a device which delivers electrical pulses having one or more tines radially deployable from the main shaft into the tissue to form an array of tines having energizeable surfaces. The tines may be individually energizeable for use in bipolar pulse pairing configurations, or all energized to the same polarity for use with a secondary device such as a surface electrode to complete the circuit. The tine style electrode device may be either single pole wherein the electrical current travels between the individual tines of the tine array and a surface electrode or may be a bipolar design wherein the electrical current travels between the uninsulated portions of selected pairs of tines. An electrode, as disclosed herein, may also refer to a dispersive pad device which is placed on the surface of the patient skin or body part to complete the electrical pathway. This type of electrode device may also be referred to a as grounding pad, dispersive pad or patient return pad.

Embodiments described herein utilize one or more combinations of HFIRE technologies into techniques for delivering HFIRE therapies for focal tissue destruction. The embodiments described herein aim to garner the benefits from each individual technology to produce an optimized method for delivering electroporation treatments. The objectives may include allowing simplicity of insertion and use, manufacturing practicality, large reliable treatment zones, spherical treatment zones, reduced thermal effects, elimination of complications associated with arcing between electrodes, and possible elimination of the need for a paralytic.

Some embodiments may use a tine-style, single-stick electrode device, where the tines may not be electrically isolated (as required using conventional bipolar tine-style electrodes). In some embodiments, the shaft of the electrode may be insulated, and tines may be advanced and retracted as needed by the user. The electrode device may electrically communicate with an electroporation generator that includes a controller to generate high frequency irreversible electroporation (HFIRE) pulse protocols to deliver electrical pulses without enacting significant muscle twitch, and the system may use at least one skin or organ surface external electrode to complete the circuit through a patient's tissue, and may create large spherical ablations.

While the combination of a single-pole, non-tined electrode and one or more skin surface electrodes may show great promise for generating large spherical ablations, the permissible voltage and other pulse parameters may become limited by the nature of delivering strong electric pulses through a larger portion of the body, which may increase muscle activation. For traditional IRE pulse protocols, muscle activation has proved prohibitive in experimental in vivo trials, where clinically useful IRE zones may cause muscle contractions that cannot be reasonably attenuated with traditional muscle-blockade. Conversely, HFIRE protocols have been shown to create ablative lesions without significant muscle contractions, thus eliminating or reducing the need for paralytics, as described in U.S. patent application Ser. No. 13/332,133, which is incorporated herein by reference. However, HFIRE parameters are known to create much smaller lesions than standard IRE which may not be clinically acceptable. Accordingly, there is a need to provide a system and methodology that will create large lesion volumes using a single probe device which can be easily and accurately placed while eliminating or minimizing the need for systemic paralyzing agents to control muscle contractions during the procedure.

Referring now to FIG. 1, an embodiment of an electrical generator system 100 and method of use is illustrated. In one embodiment, the HFIRE system 100 may comprise one or more components. Although the HFIRE system 100 shown in FIG. 1 has a limited number of elements in a certain topology, it may be appreciated that the HFIRE system 100 may include elements in alternate topologies as desired for a given implementation. HFIRE system 100 includes a high-voltage generator 108 capable of generating HFIRE pulses, at least one single-pole tine-style electrode probe 101 connectable to generator 108 by cable 214. The system 100 may also include an external surface electrode 112 which may be placed on the skin of patient 132 and is connectable to the generator 108 by cable 215. In one embodiment of use, the probe 101 is inserted into the patient at the targeted area and the tines are deployed into the target tissue 216. The surface electrode 112 is placed on the patient's skin as the other electrode in the pair for creating a closed electrical circuit through the patient's body, as shown by arrow 134. HFIRE energy delivered between the single-pole tine-style probe and surface electrode ablates the target area as the current travels between the tine probe 101 and surface electrode 112. Use of a surface electrode further reduces the need for systemic paralytics since energy is dissipated over a much larger tissue area resulting in less muscle spasms. Placement of the surface electrode to create an electrical pathway that avoids significant muscle mass may further reduce muscle contractions to a level at which systemic paralytics is no longer required. If the desired placement of the surface electrode creates an electrical pathway through significant muscle masses, paralytics may be needed.

Figure 2A:
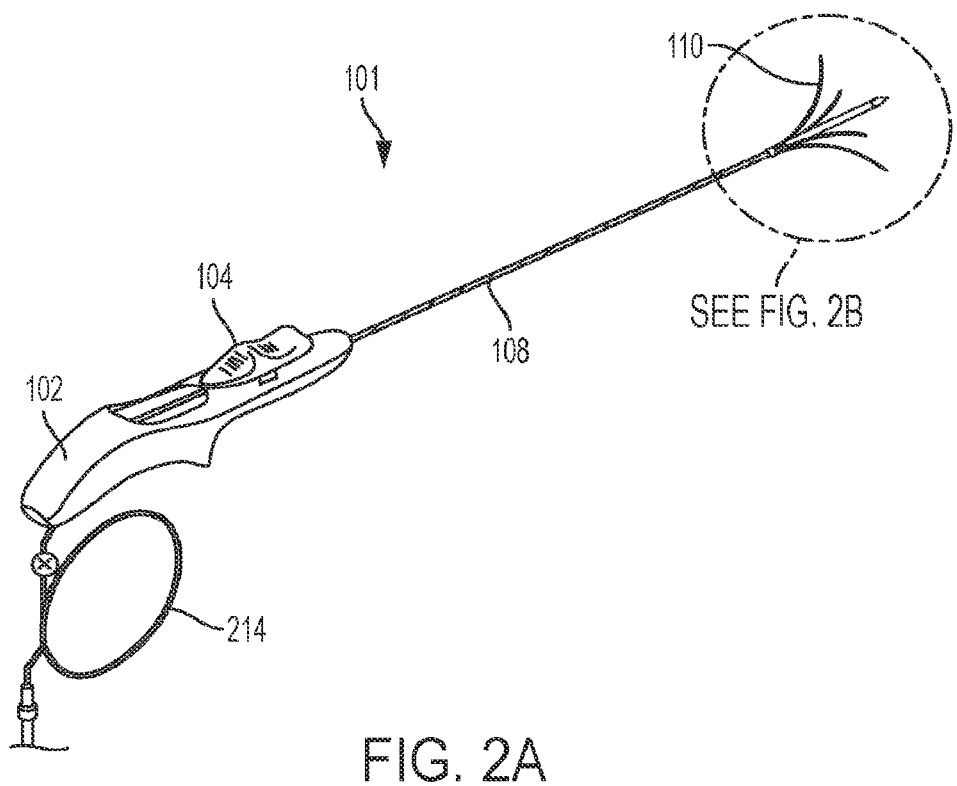
FIG. 2A illustrates an isometric view of a single-pole tined-style electrode probe according to an embodiment.
Figure 2B:
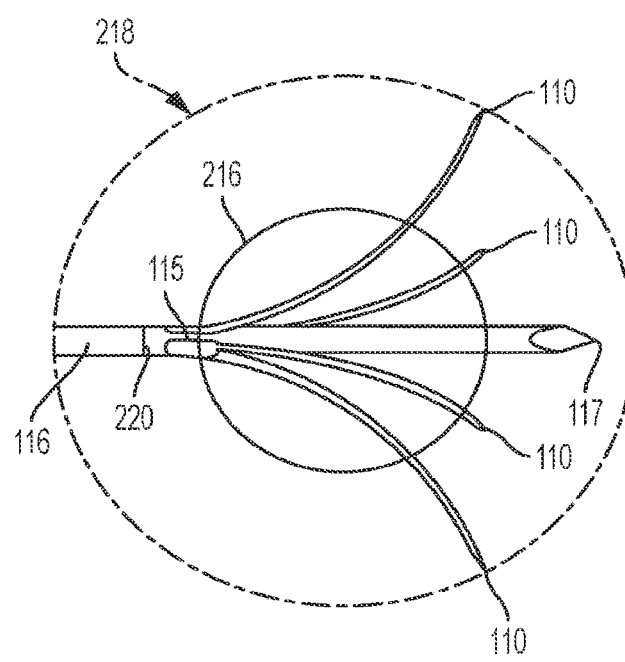
FIG. 2B illustrates an enlarged side view of the distal section of the single-pole tine-style electrode probe of FIG. 2A.

FIG. 2A illustrates an isometric view of one embodiment of the single-pole tine-style electrode probe 101 showing the tines 110 in a fully deployed position. Probe 101 may include a cable 214 for attachment to the generator 108, a handle 102 and a deployment/retraction element 104, which may be used to deploy/retract one or more tines 110 from the shaft 108 after electrode probe 101 has been inserted into a target region 216 of a patient's body. Upon activating deployment/retraction element 104, one or more tines 110 may be advanced from within a shaft 108 of electrode probe 101, and deployed into a pre-formed curvature as shown in FIG. 2B, which illustrates the distal end section of probe 101. Target region 216 may be in or near an organ, such as a liver, lung, or kidney, for example. While four deployable tines 110 are illustrated within HFIRE system 100, it can be appreciated that more or less tines, as well as various tine configurations, may be used in other embodiments. As an example, tines 110 may be arranged in a multiple tier configuration, as described with respect to FIG. 9A-9B.

FIG. 2I illustrates an enlarged, partial plan view of the distal segment of the electrode probe 101, showing the tines 110 radially deployed from the shaft 108. Shaft 108 includes an insulation sleeve 116 on its outer surface hi one embodiment, the insulation sleeve 116 is retractable. Tines 110 are deployed through shaft apertures 115 into a three-dimensional array by activating the deployment/retraction element 104. When fully deployed, tines typically extend 2-3 cm radially from the shaft 108, resulting in an ablation zone coverage diameter of 4-6 cm. In some embodiments, the tines may be designed to extend further out into the tissue, such as up to 4 cm. Additional tines and tiers may be beneficial when using longer tines to ensure a generally spherical shape and complete ablation coverage of the targeted treatment area.

The insulation sleeve ensures that the main body of the shaft remains electrically inactive. The shaft 108 terminates in a sharpened distal tip 117, which is used to facilitate percutaneous insertion into the target site. In one embodiment, the distal tip 117 and adjacent shaft may be conductive and act as a central electrically active tine. In another embodiment, the distal tip 117 may be non-conductive, partially non-conductive along a desired length or variably conductive as described in U.S. Pat. No. 9,339,328 which is incorporated herein by reference. As a non-limited example, the central shall 108 may be uninsulated from the distal edge 220 of insulation 116 to the sharpened distal tip 117. This length of the shaft 108 may thus act as an active electrode surface to enable larger ablation volumes. In one non-limiting embodiment, the exposed, uninsulated shaft is 3 cm in length with a corresponding deployed tine length of 2 cm. By designing the uninsulated portion of the central shaft 108 to be longer in length than the deployed tines, the resultant ablation zone will be more spherical in shape than when using an equally length exposure for the central shaft and tines.

During the delivery of HFIRE-specific pulses, discussed in further detail below, electrical energy flows along the insulated shaft 108, exiting through the uninsulated tines 110 of the probe and uninsulated portion of shaft 108 and then flowing toward the surface electrode. Because HFIRE pulses as described herein are bi-polar, energy alternatively flows from the surface electrode toward the deployed tines of the probe 101 and back. The concentrated distribution of electrical current surrounding the tines and exposed central shaft creates nano-pore defects in the cell located in target region 216, resulting in a generally spherically shaped ablation volume 218, which includes the target region 216 and a peripheral margin volume 218. Tines positioned in a spherical arrangement create a larger more uniform electrical field within the target tissue, when compared with a non-tined electrode probe or a bi-polar tine-style device which requires insulation of the individual tines. The single-pole tine-style device may be set to either a positive or negative polarity, or alternatively the polarity of the tine-style device and surface electrode may switch between positive and negative during energy delivery.

While four tines 110 are illustrated within electrical generator system 100, it can be appreciated that more or less tines, as well as various tine configurations, may be used in other embodiments. Typically, tines are single-tier so as to provide a spherical ablation volume, but based on the overall tumor shape and profile, other tine configurations may be used to achieve complete ablation coverage for non-spherical tumors. As an example, tines 110 may be arranged in a multi-tier pattern (described with respect to FIG. 9A-9B). In another non-limiting example, longer tines may be used in combination with a longer central shaft exposure. Further, tines may include sensor components in some embodiments, which may gather data in near real-time with respect to an ongoing HFIRE procedure, such data communicated to a processor and displayed to a user of an HFIRE system. As an example, the user may deliver a series of pulses and then review the extent of ablation using impedance, conductivity, temperature or other readings sensed by the tines before continuing the procedure. The intra-procedural treatment data may also be used to determine extent of ablation and/or the procedure endpoint.

Various configurations of electrode probe 101 may be used. For example, the electrode probe may be cooled, so as to eliminate any thermal damage to tissue in physical contact with the electrode surface or to decrease change in tissue electrical conductivity due to changes in tissue temperature. Non-limiting examples of cooling techniques that may be used include internal circulation using a closed-loop perfusion circuit to cool electrode probe 101, intra-shaft circulation to cools the delivery shaft only (possibly including active portions of delivery shaft), intra-tine circulation to cool the tines 110 of electrical energy delivery, or infusion techniques including single-path fluid delivery which exits either out of the shaft or tines directly into a patient's tissue, as is described in as described in PCT Application PCT/US2016/26998 filed Apr. 11, 2016, which is incorporated herein by reference.

In an example, an internally perfused shaft may help mitigate thermal damage and electric conductivity rise (and thus electric currents encountered by a patient). In other embodiments, an infusing device may be used in conjunction with disclosed systems to cool tissue, manipulate electric conductivity distribution, or administer chemotherapy, immunostimulants, radioisotopic solutions, or other chemicals relevant to a given procedure. In some embodiments, infusing through tines may provide desirable results over conventional infusing techniques using only single pole, non-tined electrode probe, since tines may reach a greater volume of tissue once deployed, for example.

Figure 12:
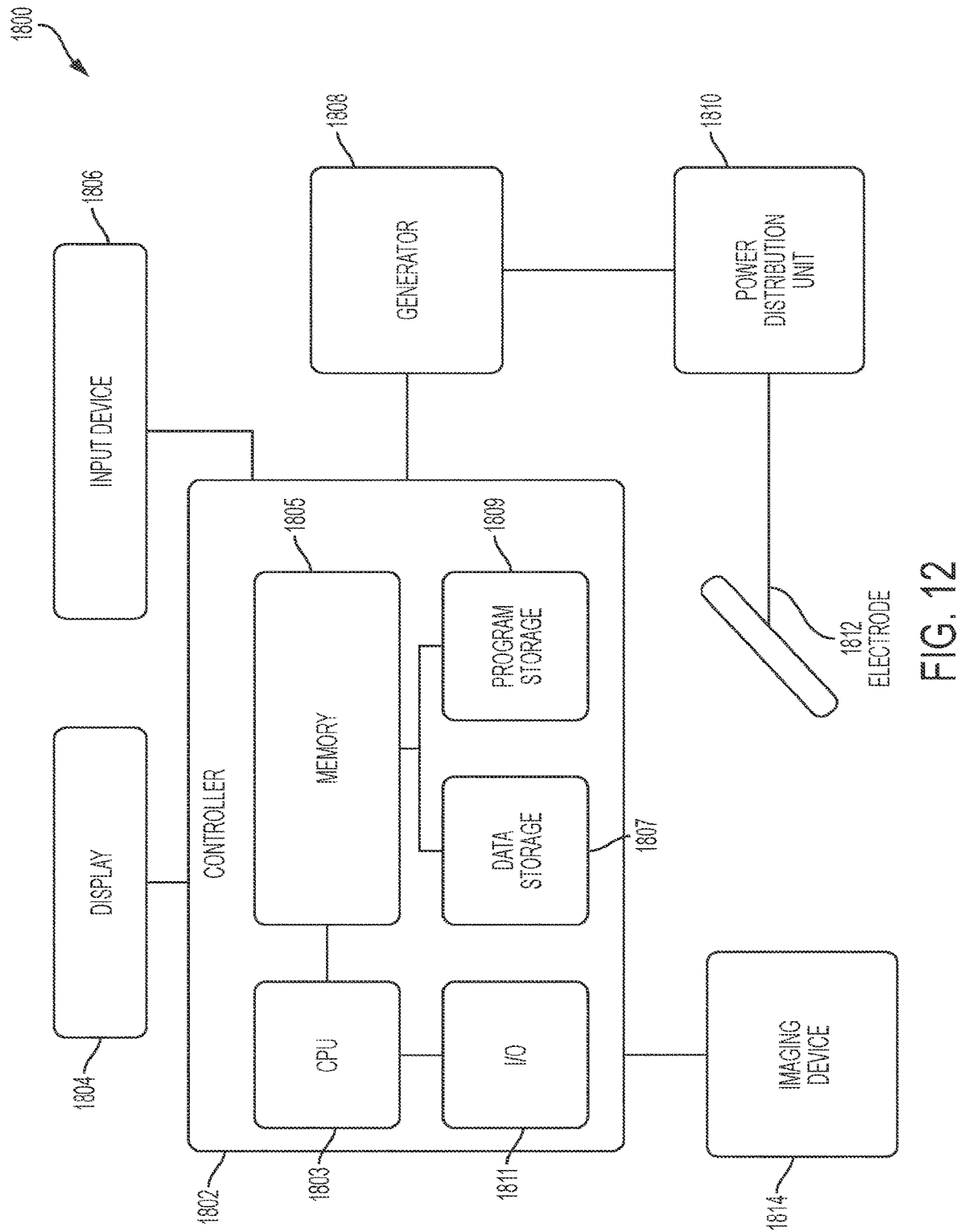
FIG. 12 illustrates a schematic of the HFIRE system according to one embodiment.

The HFIRE generator 108 may be configured to generate electrical energy pulses according to an HFIRE protocol, controlled using an electrical generator system such as that described with respect to FIG. 12, for example. Typical HFIRE treatment parameters may be within the ranges shown in Table 1 below.

TABLE 1

HFIRE PULSE PARAMETERS

| Parameter | Value |
|---|---|
| Output Voltage | 2,000 V-10,000 V |
| Burst Width | 500 nsec-1 msec (typically 100 μsec) |
| Inter-burst Delay | 1 msec-5 sec (typically 1 sec) |
| Pulse Width | 100 nsec-10 μsec (typically 5 μsec) |
| Interpulse Delay | 100 nsec-1 msec (typically 10 μsec) |
| Pulses Per Burst | 2-100 |
| Bursts Per Treatment Set | 50-400 (typically 200 bursts) |
| Total Treatment Time | 50-400 seconds (typically 200 seconds) |
| Pulse Type | Bi-phasic |

Figure 11:
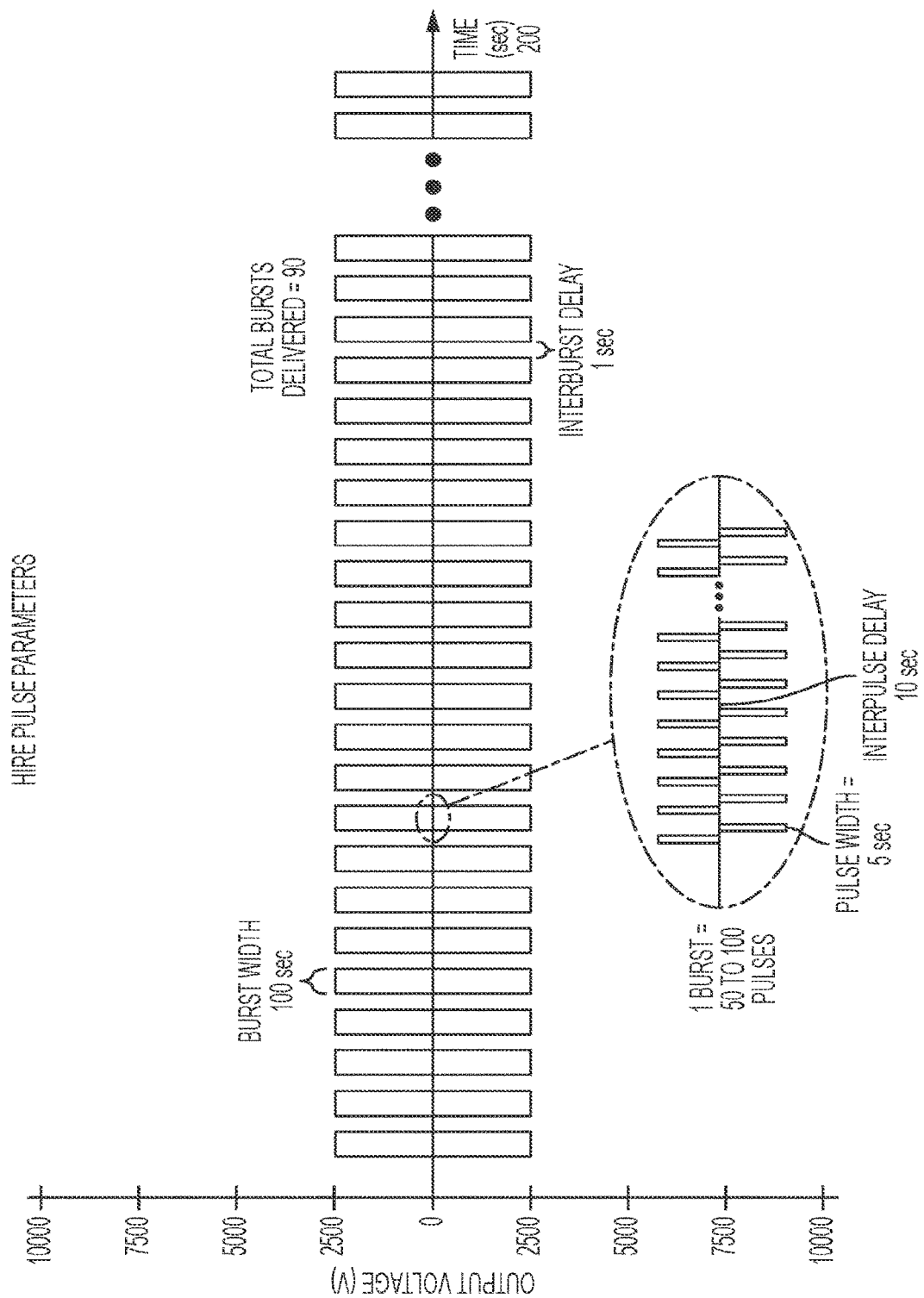
FIG. 11 graphically depicts HFIRE electrical protocol parameters associated with a treatment protocol according to one embodiment.

FIG. 11 graphically illustrates HFIRE pulse parameters of one non-limiting embodiment. As shown, the output voltage of the bipolar pulses is 2500 V (+/−) and consists of a pulse train sequence (if 200 bursts. The duration of each burst is 100 μsec (burst width) with a 1 second delay between each burst. A single burst is comprised of between 5 and 100 alternating positive and negative pulses. The duration of each pulse is 5 μsec long (pulse width) with a 10 μsec delay between each pulse.

Using pulse parameters within the range described above provides key advantages when used with a single-pole tine-style electrode and external surface electrode. Compared with a single, non-tined probe, the system described herein may utilize higher ampere (50 A or above) and voltages levels (2 kV and above) with longer active pulse duration due to the line-to-surface electrode design, which accommodates larger energy flows than a single pole, non-tined device. In addition, larger, more spherical ablations are created using the tine style device than with non-tined electrode HFIRE protocols, as will be explained in further detail below. In yet another advantage, the tined electrode/surface electrode setup creates larger ablation volumes with less thermal damage than a non-tined electrode using identical energy delivery parameters. Thus, using the same energy delivery parameters, the tine-style probe device provides larger, safer ablation zones compared with the non-tined probe device.

Using single-pole tine-style electrode probe positioned in a spherical arrangement creates a larger, more uniform electrical field within the target tissue than the electrical fields generated by a bipolar tined probe or by multiple single pole probes. Because the single-pole tines are interacting only with the surface electrode and not each other, consistent uniform positioning of individual tines relative to each other is not as critical as with bipolar tine embodiments. Thus, the tines may become "misaligned" during deployment and still will be able to perform their function. As an example, a 2-3 mm deflection of a single tine of a bipolar tine device may result in arcing between the active tine pair which in turn may result in a high-current system failure, localized thermal damage, and/or incomplete ablation coverage. Accordingly, this invention eliminates the time consuming procedural steps of retracting, repositioning and redeploying misaligned tines prior to the application of electrical current.

Another known problem with bipolar tined electrode devices is the unequal energy disposition in the targeted treatment site. When a bipolar tine array is deployed into its final expanded position, the distance between the tines is not parallel along the entire deployment length but instead varies, with the distance between any two tines being the greatest at the distal ends, which extend furthest into the tissue. The energy flow will be the strongest at a point which represents the shortest distance between the tines and will decrease as the distance between the exposed tines increases. This uneven energy distribution pattern can lead to incomplete treatment at the periphery of the targeted tissue volume and overheating or electrical current overload at the proximal section of the active tines. Using the device and method of the current invention eliminates this problem by using a surface electrode in conjunction with a single-pole tine-style electrode probe to create spherical, homogeneous ablation zones with uniform electrical field distribution, whereby the radial spacing of the tines relative to each other is not a critical factor in successful energy delivery.

This invention also eliminates the time-consuming steps involved with positioning multiple single pole electrode probes in a parallel arrangement. If the active electrode surfaces of two single-pole electrode probes are not parallel along the entire length of the active electrode surface, the resulting ablation may be irregular in volume and space with localized thermal damage, particularly where the electrode surfaces are closer to each other than desired. To ensure substantial parallel placement (typically within a tolerance of 3 mm or less), the user must carefully plan probe placement, confirm correct spacing along the length of the probes during insertion using imaging technologies, and reposition one or more probes if misaligned. These steps are the most time-consuming aspect of a radiational IRE procedure. By using an HFIRE protocol and a single-pole, tine-style electrode device with a corresponding surface electrode, the time spent placing the probe is reduced to a single insertion stick and subsequent tine deployment in the central region of target tissue. Misalignment of individual tines relative to each other is not critical since the electrical current flows between the surface electrode and tines. If desired, any misalignment of tines can be corrected by retraction of the tines into the shaft, repositioning of the probe, followed by redeployment of the tines.

Using the HFIRE probe configuration described herein, the pulse delivery may not encounter the traditional problems that have plagued single needle and tined probes configured for bipolar energy delivery. Arcing and high-current failures, as well as technical device complexity associated with bipolar tined devices are eliminated. The ability to generate very large (approximately a 5 cm diameter in some exemplary embodiments) lesion zones becomes predominantly a function of pulse generator capacity for an HFIRE procedure. With a sufficiently large surface electrode, the concentration of voltage gradient at the electrode may be sufficient for generating a useful lesion, while diffusing sufficiently at the surface electrode to prevent significant onset of non-targeted electroporation and/or thermal burns at the surface electrode. Thus, a single-pole tine-style electrode and skin surface electrode combination may serve as a promising approach to delivering HFIRE procedures in a simple-to-deploy and easy to deliver protocol with clinically useful HFIRE zones.

While HFIRE system 100 includes a single skin surface electrode 112, other configurations may be used. For example, the size of skin surface electrode 112 may be larger or smaller based upon a desired result In an exemplary embodiment, one small external electrode may have more concentrated electric energy delivery communication. In another embodiment, one large external electrode may be used to diffuse electric energy path, mitigating electroporation and thermal effects at the skin surface 118 as well as diffusing energy concentration to reduce the possibility of muscle contractions. In other embodiments, described below with respect to FIG. 10, several large or small external skin electrodes may be used to generate greater diffusion of the electric energy path. A skin surface electrode may be placed close to the insertion of the tine-style device. In other embodiments, one or more skin-surface electrodes may be placed at various locations around the body in a predetermined pattern, based upon desired results. Likewise, placement of one or more skin surface electrodes may be performed to reduce negative effects of an H FIRE procedure, such as away from a patient's heart to reduce cardiac risks, or placement over less muscular tissue to further reduce muscle twitch. In some cases, particularly if the probe location is of sufficient distance from the heart, the need for a separate cardiac synchronization protocol may not be required, as is typically required with IRE procedures to mitigate adverse cardiac events.

In some embodiments, additional devices may be used to interface with an external surface electrode. Additional devices may be chosen based upon a variety of criteria, such as for specific procedures, or results. For example, an intraluminal device with a surface electrode may be used for any number of intraluminal applications such as procedures on the urethra, esophagus, bronchus, or intestines. The intraluminal device may take the form of an electrode balloon or an expandable cage that contacts the tubular wall for delivery of electroporation pulses. An intraoperative flat electrode net or pad nay be placed on the target tissue surface. In these embodiments, a surface electrode is used in conjunction HFIRE pulse parameters to achieve more effective ablation zones with minimal muscle contractions.

The combination of these technologies ((HFIRE, single-pole electrode probes with tines, and one or more surface electrodes) provide unique advantages delivering HFIRE focal targeted therapy with critical structure sparing. While traditional IRE with surface pad electrodes may produce large lesions, the muscle twitch is unacceptable to perform a successful procedure. While HFIRE with surface pad electrodes may dramatically reduce muscle twitch, the lesions are too small when using a single-needle style electrode.

Further, results have shown that utilizing a single-pole, line-style probe with disclosed HFIRE pulse parameter protocols may produce up to an 80% larger ablated treatment zone, which is more spherical in shape than previously known solutions. Furthermore, when compared to traditional IRE pulses, the configuration disclosed herein dramatically reduces the thermal implications at the temperature realms that risk damage to critical structures by 60% to 100% from thresholds of 55° to 70° C., as will be discussed in further detail below. It should be noted that these thermally affected volumes are smaller than those shown for single-pole electrode pair pulse protocols. While temperatures may increase for higher voltages applied, it is also possible to further increase the HFIRE treatment zones by moving to higher voltages.

Still referring to FIG. 2B, shaft insulation 116 terminates at edge 220. Since during energy delivery each tine interacts with the surface electrode 112 rather than with other tines on the probe, the tines do not require any type of electrical insulation. It has traditionally been technically challenging to individually insulate tines, particularly deployable tines, which are susceptible insulation damage as the tine moves from an undeployed position within the shaft to an expanded position within the target tissue. The insulation sleeve required for each tine also results in a larger overall device size. However, HFIRE systems described herein may include tine designs without an insulating layer. In this manner, embodiments described herein are advantageous relating to the ease of manufacturing, overall smaller diameter and device dependability.

In addition to simplifying device construction, embodiments described herein utilizing tines that are not electrically isolated may dramatically reduce procedure set up and pulse delivery time by eliminating the tine-pair permutations typically needed when using insulated, bi-polar tine designs. For example, a bipolar electrode probe with four tines and an active central shaft may need up to five physical connections to an electrical generator, one for each active tine. In contrast, the device and method of this invention requires a single connection between the electrode probe 101 and generator 108, and a second physical connection between the surface electrode 112 and generator 108.

Figure 3B:
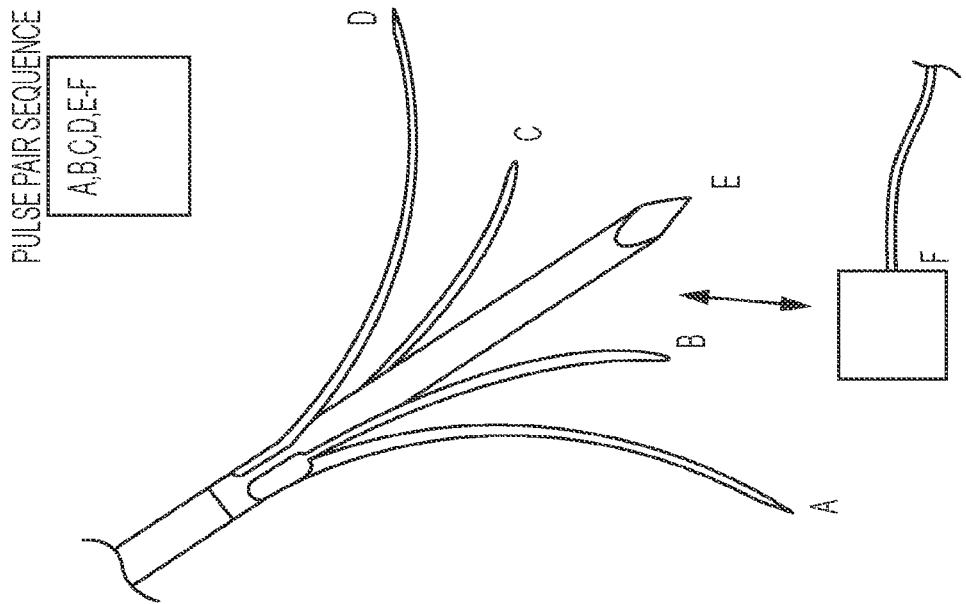
FIG. 3B illustrates a distal section of a single-pole tine-style electrode probe and surface electrode depicting a pulse pair sequence according to one embodiment.
Figure 3A:
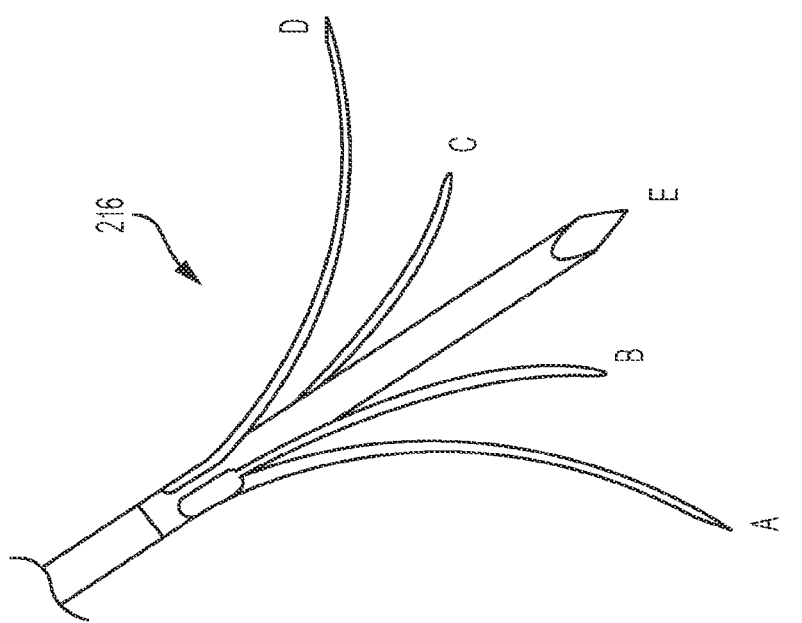
FIG. 3A illustrates a distal section of a bipolar tine-style electrode probe depicting a pulse pair sequence.
Figure 9A:
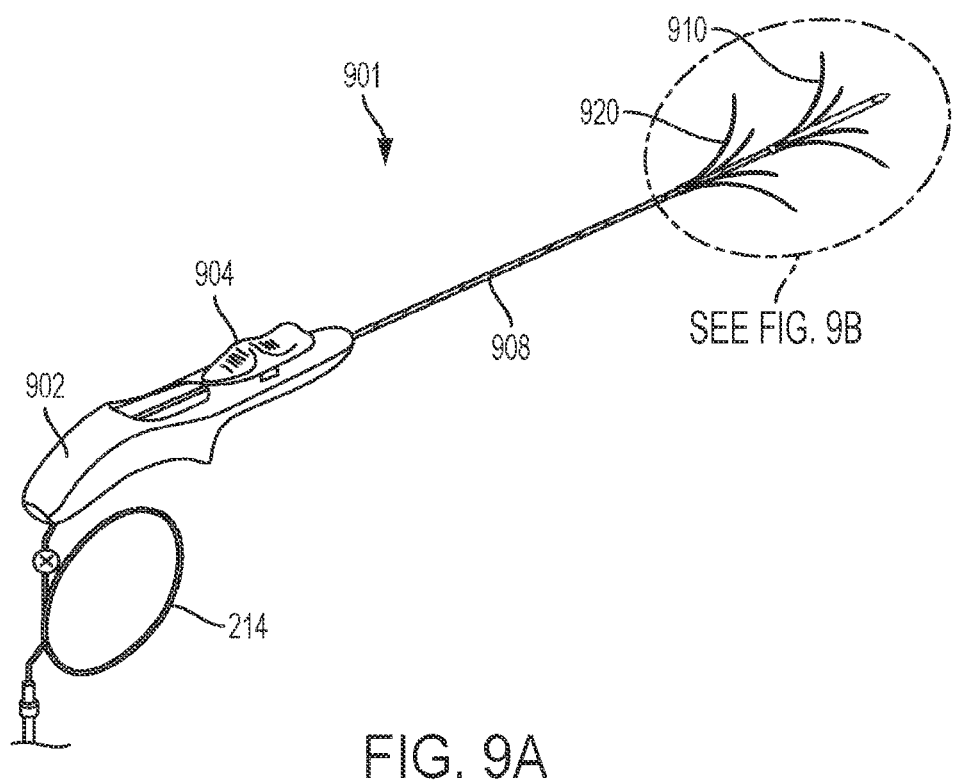
FIG. 9A illustrates an isometric view of an embodiment of a single-pole tine-style electrode probe with two tiers of tines.
Figure 9B:
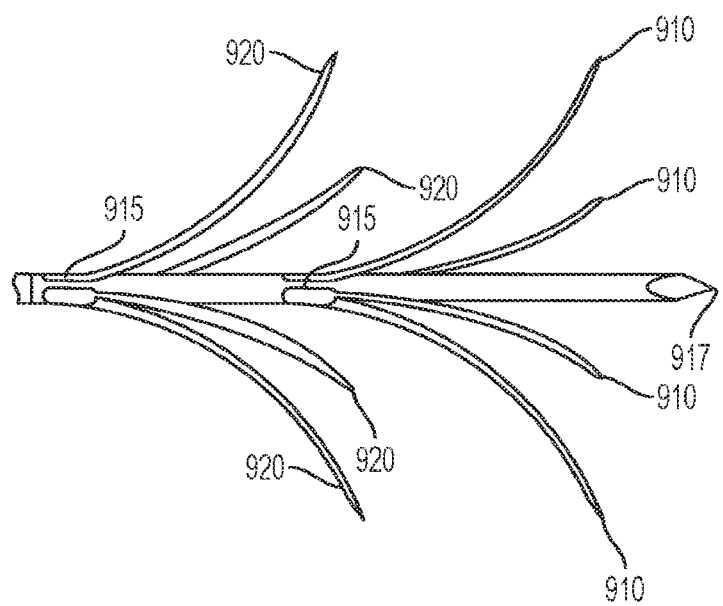
FIG. 9B illustrates an enlarged side view of the distal section of the two-tiered, single-pole tine-style electrode probe of FIG. 9A according to an embodiment.

Pulse delivery time is also shortened with this invention due to the reduced number of electrode pairing permutations, as illustrated in FIG. 3A-3B. FIG. 3A depicts a typical pulse pair sequence for a bipolar probe with partially insulated tines In this configuration, electrical pulses flow between a designated pair of tines (labeled A, B, C, D) and/or a tine and the uninsulated part of the central shaft (labeled E), before switching to a different pair. The number of pairings required to cover the target tissue using a four-tined, bipolar device is ten, as shown in the Pulse Pair Sequence box. However, as shown in FIG. 3B, utilizing tines that are not electrically isolated require only a single pairing between the surface electrode, labeled F and the multiple electrically active surfaces of the tines, labeled A-E. By eliminating complicated tine pair switching algorithms and the time required to cycle through each tine pair multiple times as required by the HFIRE protocol parameters for bipolar tine devices, the actual procedure time may be reduced by up to ten-fold. This advantage multiples exponentially when using a multi-tiered device as shown in FIGS. 9A and 9B.

Figure 4B:
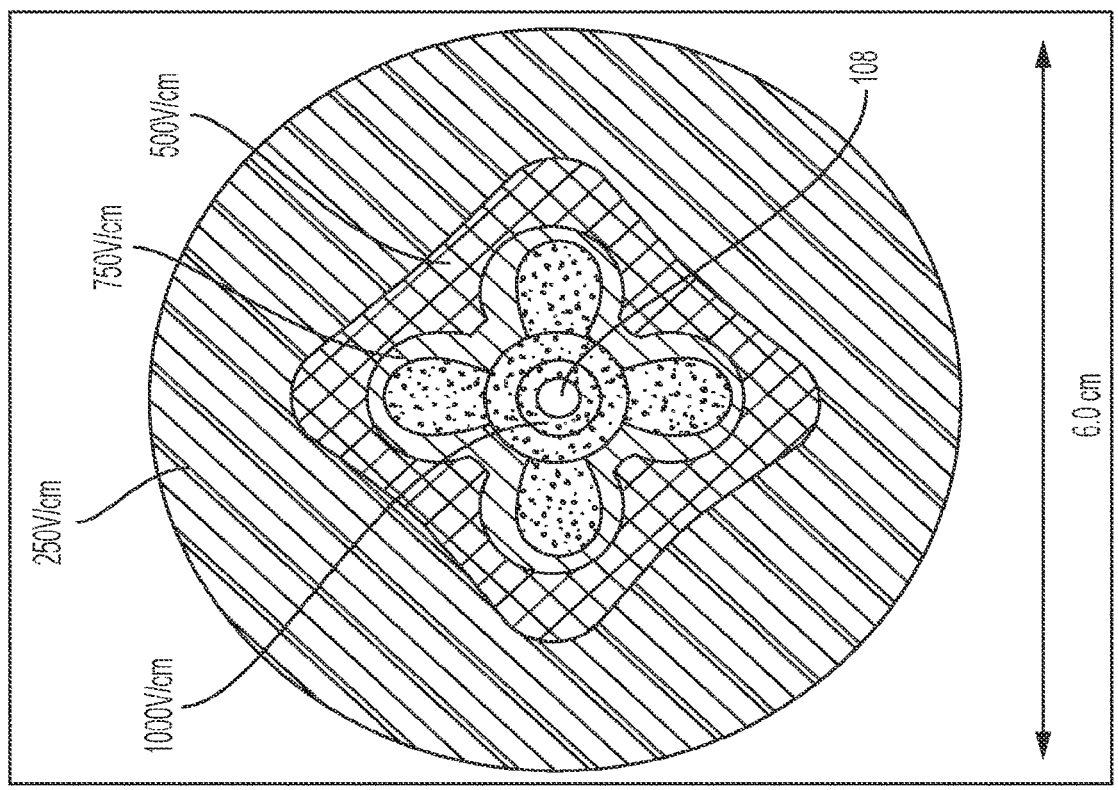
FIG. 4B graphically illustrates an electrical field distribution after application of 100 HFIRE pulses using a single-pole line-style electrode probe according to an embodiment.
Figure 4A:
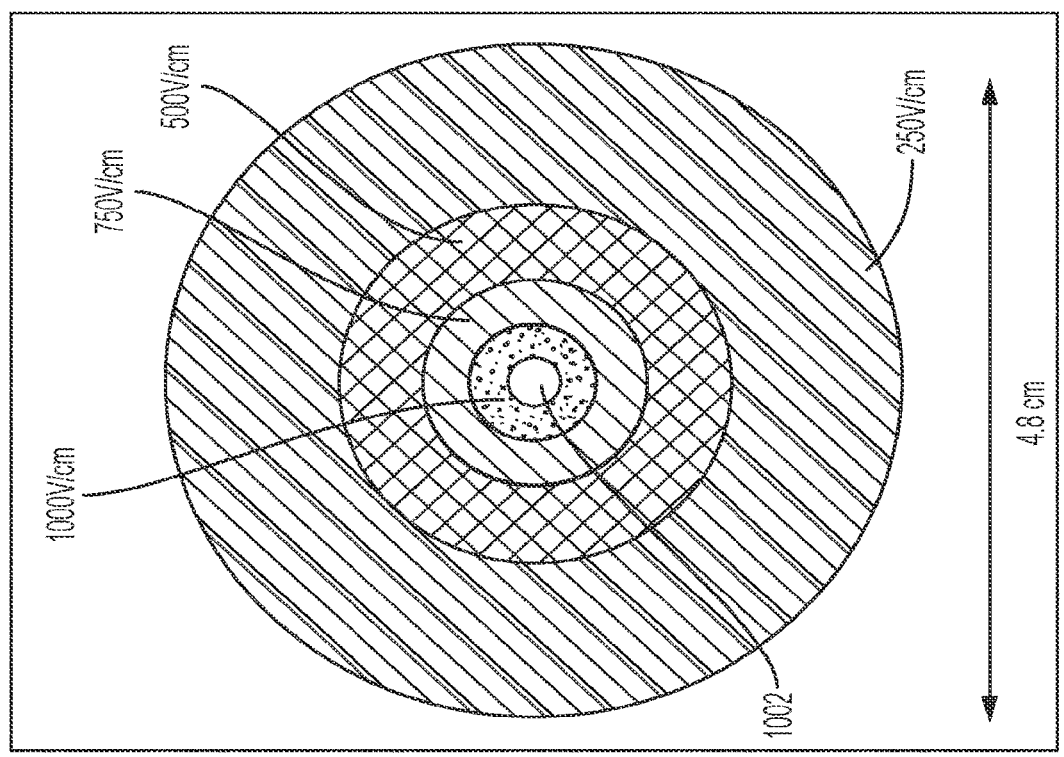
FIG. 4A graphically illustrates an electrical field distribution after application of 100 HFIRE pulses using a single-pole non-tined electrode probe.

FIGS. 4A and 4B graphically compare electric field distributions generated using a single-pole, non-tined electrode probe (FIG. 4A) and a single-pole, tine-style electrode probe 101 (FIG. 4B) after application of 100 bi-polar HFIRE pulses. Specifically, the graphs illustrate tissue exposure to selected HFIRE electrical field thresholds using 3000V pulses for a single-pole non-tined electrode probe with a 2 cm shaft exposure and a single-pole four-tine style electrode probe 108 with 1 cm tine exposure, including a 1 cm exposure on the main shaft from insulation edge 116 (see FIG. 2B) to distal end 117. The non-tined electrode probe produced lesion diameter of 2.6 cm and 4.8 cm for 500 V/cm and 250 V/cm electrical field thresholds, respectively. In contrast, the four-tine electrode probe in conjunction with a surface electrode produced diameters of 3.4 cm and 6.0 cm lesions for 500 V/cm and 250 V/cm thresholds, respectively. These larger diameters represent increases of 31% and 25% for the 500V/cm and 250 V/cm thresholds. Thus, the single-pole 4-tine electrode probe with surface electrode was found to create significantly larger diameter ablation zones within each selected electrical distribution threshold value than the non-tined electrode probe.

In addition to the cross-sectional diameter of the ablation zone shown in FIGS. 4A and 4B, data on the overall volume of tissue exposure to the selected electric field thresholds were compiled and are shown in Table 2, set forth below.

TABLE 2

100 PULSE ELECTRIC FIELD EXPOSURE VOLUMES

| Electric Field Threshold | Single Probe Volume Exposure | Four-Tine Probe Volume Exposure | Percent Volume Increase with Four-Tine Probe |
| --- | --- | --- | --- |
| 250 V/cm | 72 cm$^3$ | 133 cm$^3$ | 84% |
| 500 V/cm | 13 cm$^3$ | 23 cm$^3$ | 81% |
| 750 V/cm | 4 cm$^3$ | 6 cm$^3$ | 59% |

Figure 5:
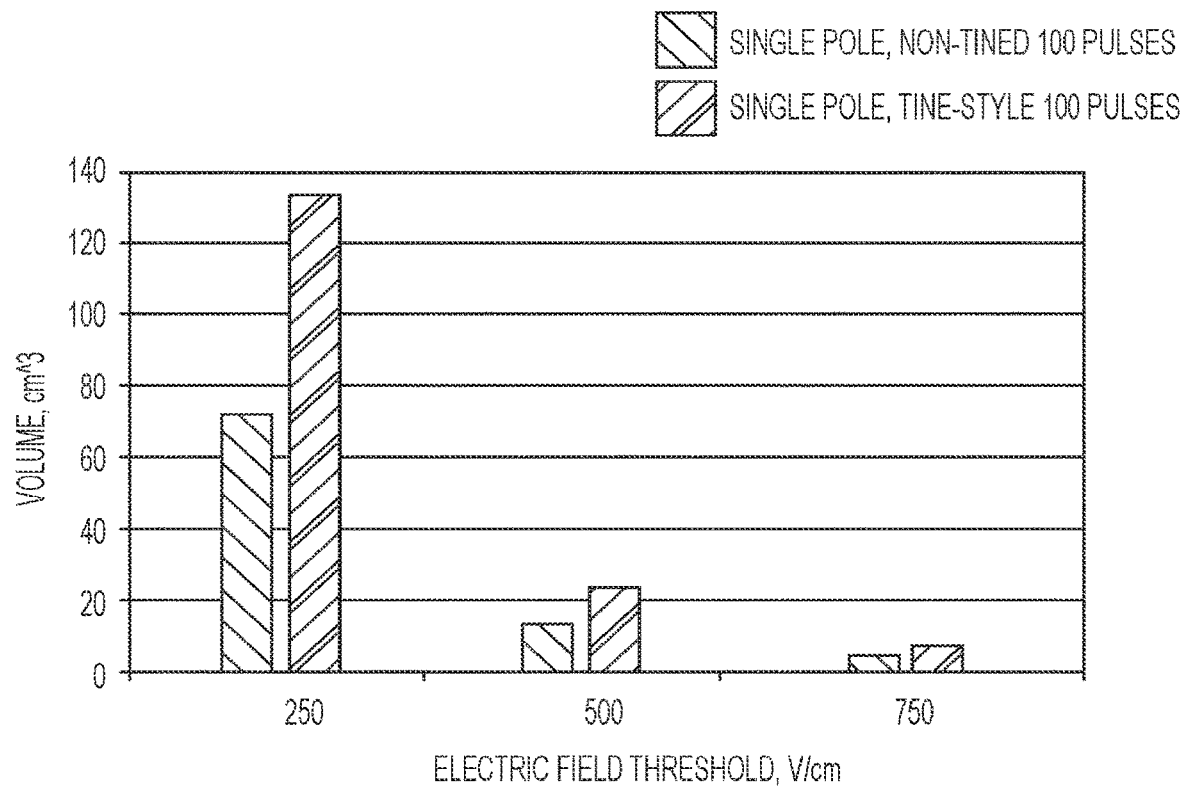
FIG. 5 illustrates ablation volumes at different electrical thresholds for a single-pole non-tined electrode probe and a single-pole tine-style electrode probe after the application of 100 HFIRE pulses.

Referring to Table 2 above and FIG. 5 which graphically illustrates data in Table 2, the single-pole, tine-style device attained significantly larger ablation volumes than the single-pole, non-tined probe device with a surface electrode using the same HFIRE parameters. At the 750 V/cm electrical field distribution threshold, the tine-style probe produced a 59% larger ablation volume than the non-tined electrode design, with an even larger increase of 81% for at the 500 V/cm threshold. At the 250 V/cm electrical distribution threshold, which represents the minimum level at which irreversible electroporation will occur, the tine-style device created an 84% increase ablation volume than the non-tined electrode design.

Figure 6:
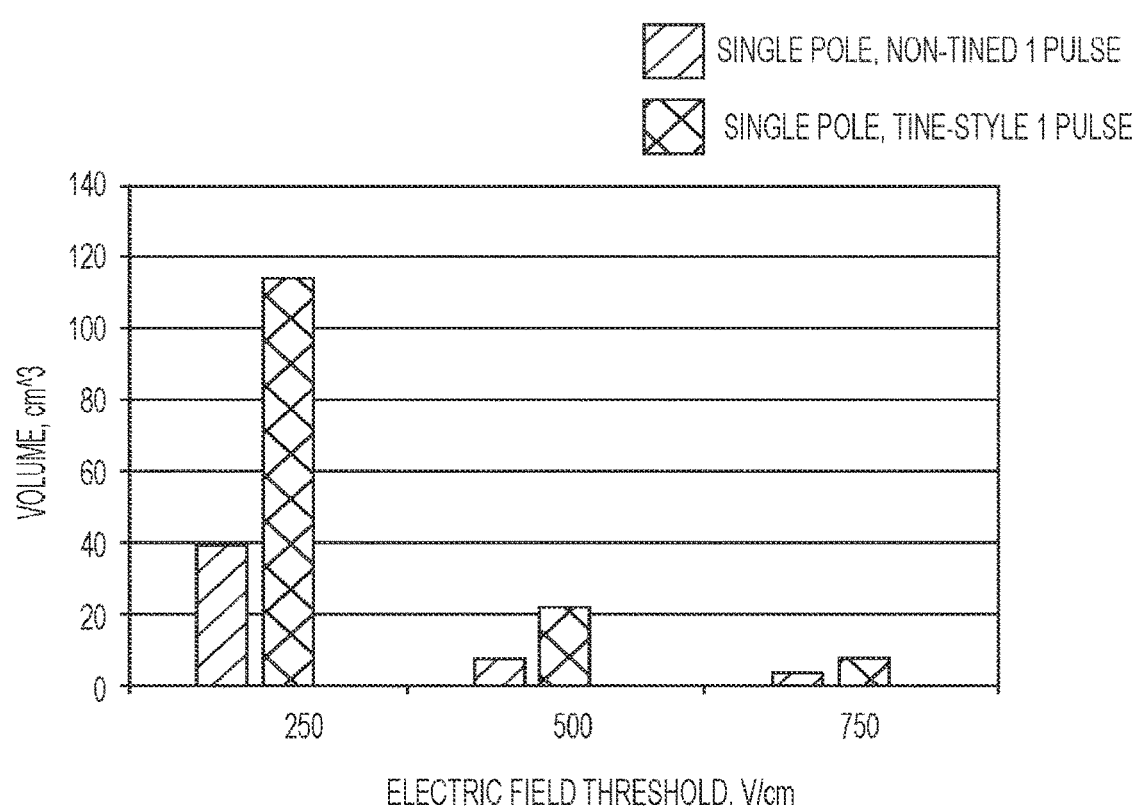
FIG. 6 illustrates ablation volumes at different electrical thresholds for a single-polar non-tined electrode probe and a single-pole tine-style electrode probe after the application of a single HFIRE pulse.

Interestingly, even a single pulse using the 4-tine electrode probe with a surface electrode was found to create significantly larger ablation zones than a non-tined design within each selected electrical distribution threshold value as shown in Table 3 below and FIG. 6:

TABLE 3

SINGLE PULSE ELECTRIC FIELD EXPOSURE VOLUMES

| Electric Field Threshold | Single Probe Volume Exposure | Four-Tine Probe Volume Exposure | Percent Volume Increase with Four-Tine Probe |
| --- | --- | --- | --- |
| 250 V/cm | 39 cm$^3$ | 114 cm$^3$ | 194% |
| 500 V/cm | 7 cm$^3$ | 21 cm$^3$ | 188% |
| 750 V/cm | 3 cm$^3$ | 7 cm$^3$ | 162% |

It is postulated that the inherent baseline electrical field distribution for the tine-style design is markedly more pronounced for a single pulse at least partially due to the physical location of the tines which extend further into the target tissue volume, with their entire surface area being electrically active. The gains from dynamic electric conductivity to the overall electric field coverage are less pronounced for the tined device. Despite this, as FIG. 5, FIG. 6 and Table 3 above indicate, four-tined probe device always outperforms the non-tined device in terms of total volume exposed to clinically relevant electrical field thresholds.

Figure 7A:
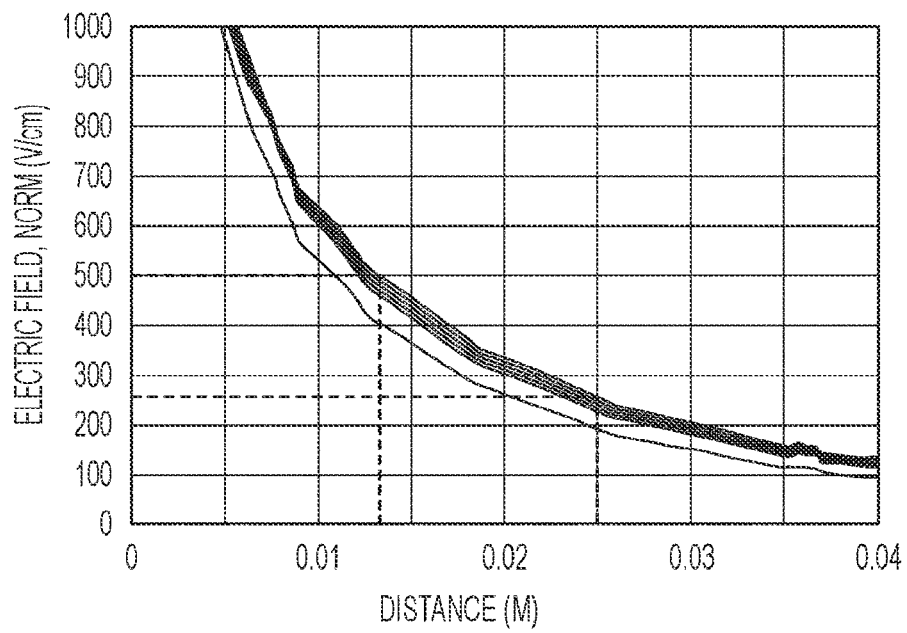
FIG. 7A graphically depicts electric field curves as a function of distance from the probe shall using a single-pole non-tined electrode probe.
Figure 7B:
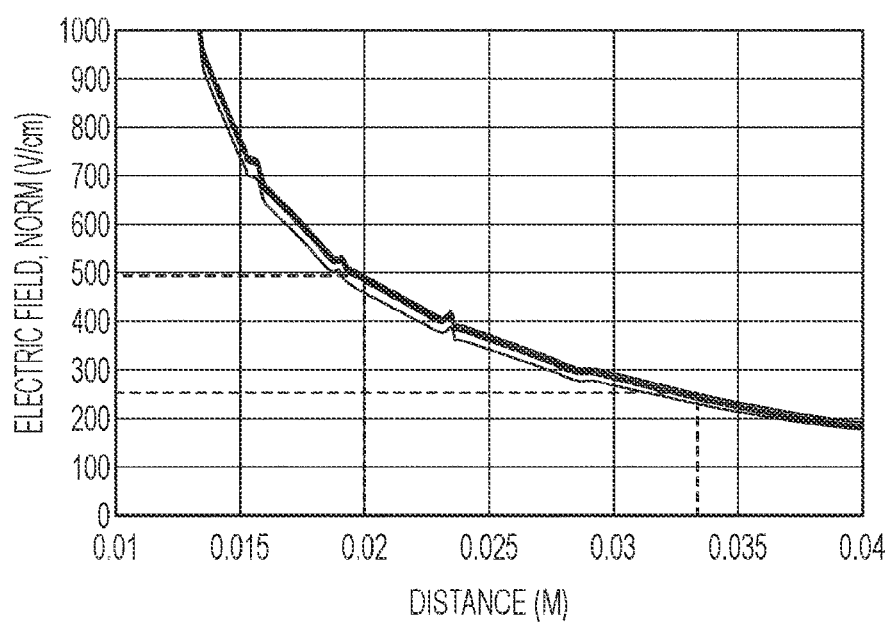
FIG. 7B graphically depicts electric field curves as a function of distance from the probe shaft using a single-pole tine-style electrode probe with corresponding external surface elect ode.

FIG. 7A-7B depict electric field curves as a function of distance from the probe shaft. FIG. 7A depicts the curves produced by the non-tined probe device and FIG. 70 shows electrical field curves produced when using a four-tine device with a surface electrode, as previously described. The Y axis represents the electrical field in V/cm and the X axis represent the distance from the center of the electrode shaft (0) in meters. Each line on the graphs represent a threshold reading at an instant in time (seconds), with a total of 135 seconds representing the approximately time required to deliver 100 pulses. Using 500 V/cm as the Y-axis reference point, the maximum penetration distance using the HFIRE pulse algorithm previously described, is 0.013 meters (1.3 cm) for the non-tined needle electrode. This compares with 0.019 meters (1.9 cm) for the tined electrode device. Thus. The tined electrode configuration results in a 0.6 cm larger ablation radius distance. When this length is doubled to account for overall length diameter of the electrical field distribution, the resulting increase in ablation cross-sectional length is 1.2 cm (from 2.6 to 3.8 cm), or a 46% increase. Using 250 V/cm as the Y-axis reference point, the resulting increase in ablation length rise to 35% (4.8 cm for the non-tined needle electrode compared with 6.0 cm for the tined electrode device).

The increased ablation volumes and treatment limiting diameters achieved when using a single-pole tine-style probe with surface electrode and previously described HFIRE protocol provides significant clinical advantages relative to the non-tined probe, bipolar configuration. As a specific example, a typical tumor size of 3 cm with a 1 cm margin requires a minimum ablation diameter of 5 cm (1 cm margin+3 cm tumor+1 cm margin). The non-tined electrode produces a 4.8 cm diameter at 250 V/cm threshold which is insufficient to achieve the desired 5 cm ablation diameter, whereas the single-pole tine-style device with surface electrode will achieve an ablation zone diameter exceeding the 5 cm. Thus, the ability to generate clinical large lesion zones (greater than 5 cm diameter) becomes predominantly a function of pulse generator capacity. When used with a surface electrode, the concentration of voltage gradient at the single-pole probe is sufficient for clinically useful lesions, while diffusing sufficiently at the surface electrode to prevent significant onset of irreversible electroporation or thermal burns in the area of the surface electrode.

Yet another advantage of embodiments described herein is the lower thermal damage profile of the tissue. As shown in Table 3 below and FIG. 8, the 4-tine electrode probe with skin surface electrode was found to create significantly lower destructive thermal zones compared with the non-tined probe device. Although the volume of tissue reaching a temperature of 50° C. was substantially equivalent for both devices types, the volume of tissue reaching temperatures above 55° C. which is above the threshold at which thermal tissue damage is initiated, was found to be 60% less for a tined-device than a single non-tined probe (2.0 cm$^3$ compared with 0.8 cm$^3$). As shown in Table 4 below, the thermal impact for the non-tined electrode becomes even more pronounced at higher temperature thresholds. At a 70° C. temperature threshold, which is the temperature at which thermal damage to the extra-cellular matrix begins, the tine-style device demonstrated a 96% volume reduction over the non-tined device.

TABLE 4

TEMPERATURE/VOLUME DISTRIBUTION

| Temperature Threshold | Volume of Exposure Single-Needle | Volume of Exposure Tine-Device | % Change in Exposure Volume |
|---|---|---|---|
| 50° C. | 3.0 cm³ | 3.0 cm³ | 0% |
| 55° C. | 2.0 cm³ | 0.8 cm³ | −60% |
| 60° C. | 1.4 cm³ | 0.3 cm³ | −81% |
| 70° C. | 0.8 cm³ | 0.030 cm³ | −96% |

Figure 8:
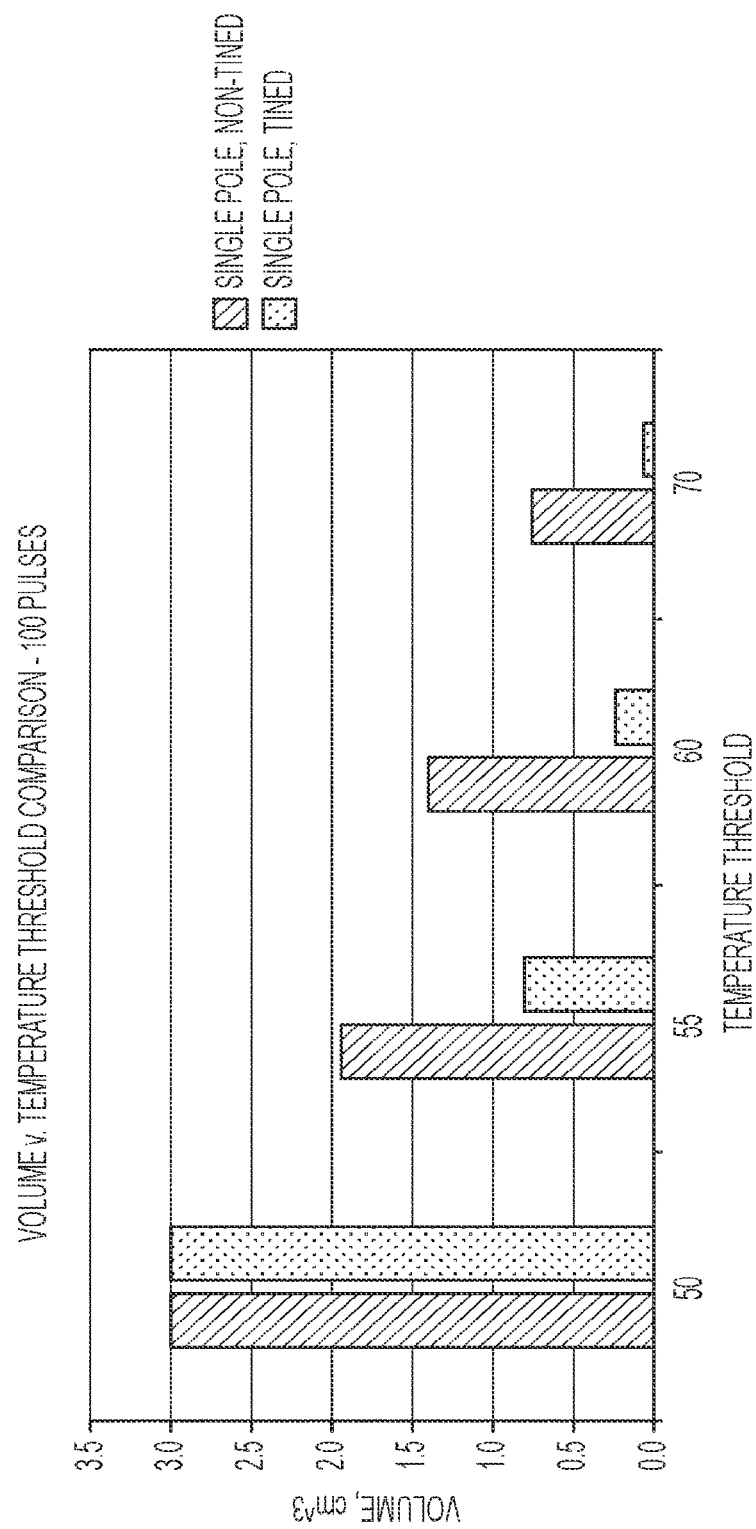
FIG. 8 graphically illustrates ablation volumes at specific temperature thresholds using a single-pole non-tined electrode probe and a single-polar tine-style electrode probe with corresponding external surface electrode.

FIG. 8, which illustrates the temperate threshold (V/cm) at various temperatures between 50'C and 70° C. using a non-tined probe and a tine-style probe, shows that although the two devices have similar volumes reaching 50° C., significantly more tissue volume is exposed to elevated temperatures with the non-tined probe. The lower thermal footprint of the tine-style devices results from the greater surface area of the tines, which disperse the delivered energy over a larger tissue volume, resulting in a more evenly distributed, and lower overall heat profile. Thus, for the tine-style configuration, a larger volume is subjected to small (≤10° C.) changes in temperature, but considerably lower volumes are exposed to more significant (>10° C.) temperature changes, particularly those in the 70° C. realm, where the onset of collagen extracellular protein denaturation becomes pervasive. A comparison of volume of treated tissue reaching 70° C. or higher for the single pole, tine style device and the single pole, non-tined devices is shown in Table 5 below and clearly illustrates the significant difference in thermal profiles of the two devices, especially in relation to the percentage temperature damage related to a corresponding IRE zone.

TABLE 5

ABLATION VOLUME REACHING 70° C. THRESHOLD

| Device type | Volume exposure at 500 V/cm | Volume exposure at 70° C. or higher | Volume exposed to thermal damage relative to IRE Volume |
|---|---|---|---|
| Non-tined | 13 cm³ | 0.8 cm³ | 0.062³ |
| Tine-style | 23 cm³ | 0.03 cm³ | 0.001³ |

The percent thermal damage is over fiftyfold higher when using a non-tined device. Thus, despite considerably larger HFIRE-affected zones of electric field exposure, the tine-style (versus non-tined probe) to surface electrode setup will result in a lower thermal profile with only minimal or no damage to adjacent non-targeted structures such as blood vessels and ducts.

FIG. 9A-98 illustrate an embodiment of a multi-tiered tine probe 901, which may include a handle 902, deployment/retraction element 904, probe shaft 908 extending distally from handle 902, and cable 214 which may be attached to an electrical generator. When in an undeployed position both arrays of tines, 910 and 920 are positioned within the shaft 908 lumen. Deployment/retraction element 904 may be used to deploy one or more arrays of electrode lines sequentially or simultaneously. For sequential deployment, the distal-most tine array 910 is first deployed into the target tissue, followed by subsequent deployment of the proximal-most tine array, 920. Sequential deployment may be accomplished using a two-staged deployment/retraction element as is known in the art.

A key clinical advantage of a multi-tier array probe is that non-spherical ablations may be achieved without the user having to place multiple probes or remove and reinsert a probe to obtain complete ablation of the target tissue. In yet another advantage, the two-tiered probe design will create a more spherical ablation zone when using longer tines because longer single-array tines typical create a non-spherical, pancake shape. Having multiple tiers also provide the user with the ability to obtain larger ablations with shapes that may be customized based on the tine-deployment protocols used. As an example, after creating an ablation volume as shown in FIG. 9B, the user may retract both array tiers within the shaft lumen, reposition the device proximally, redeploy one or both tiers and ablate a not-yet treated area to create a generally oblong-shaped ablation. In yet another embodiment, the deployment/retraction element 904 may be designed to allow deployment of only selected tines within an array. Because the surface electrode is interacting with each individual tine, deployment of less than all tines does not compromise procedure success as it would when a bipolar tined device is used. Thus, non-uniform, irregularly shaped ablation volumes may be created based on the specific tumor morphology. While eight tines 910 and 920 are illustrated in FIG. 9A-9B, it can be appreciated that more or less tiers, as well as various tine configurations, may be used in other embodiments.

Further, tines may include sensor components in some embodiments, which may gather data in near real-time with respect to an ongoing HFIRE procedure, such data communicated to a processor and displayed to a user of an HFIRE system. In yet another embodiment, some tines may act as sensors only while others are used as active electrodes. According to various embodiments, an array of sensor on each radially distributed test-probe tine, or with sensors which may be deployed to the desired dimensions, and used to track when the size and shape of the electroporated zone has met or exceeded the targeted volume. As an example of utilizing the sensors, the user may deliver a series of pulses and then review the extent of ablation using impedance, conductivity, temperature or other readings sensed by the sensors on the tines before continuing the procedure. The intra-procedural treatment data may also be used to determine extent of ablation and/or the procedure endpoint.

In one embodiment, one or more tine sensor components may use intermittent delivery of low-voltage test pulses or low-voltage AC-spectroscopy signal analysis, performed by a sensor logic executed by processing module, which may be a combination of hardware and software. Sensor logic may be configured to deliver low-voltage test pulses or low-voltage AC-spectroscopy signals between a series of electric pulses generated by HFIRE generator (other HFIRE protocols may be used in various embodiments). In this manner, the processing module may determine in near real-time whether an ablation zone is sufficient. A determination may be displayed to a user of an HFIRE system via a user interface of a display, or other user interface techniques described herein. If the zone is found sufficient, pulse delivery may be manually or automatically ceased. If the zone is found insufficient, then the voltage applied to the electrode or electrode array may be manually or automatically increased, or more pulses can be delivered, until reaching the targeted size of ablation zone.

Figure 10:
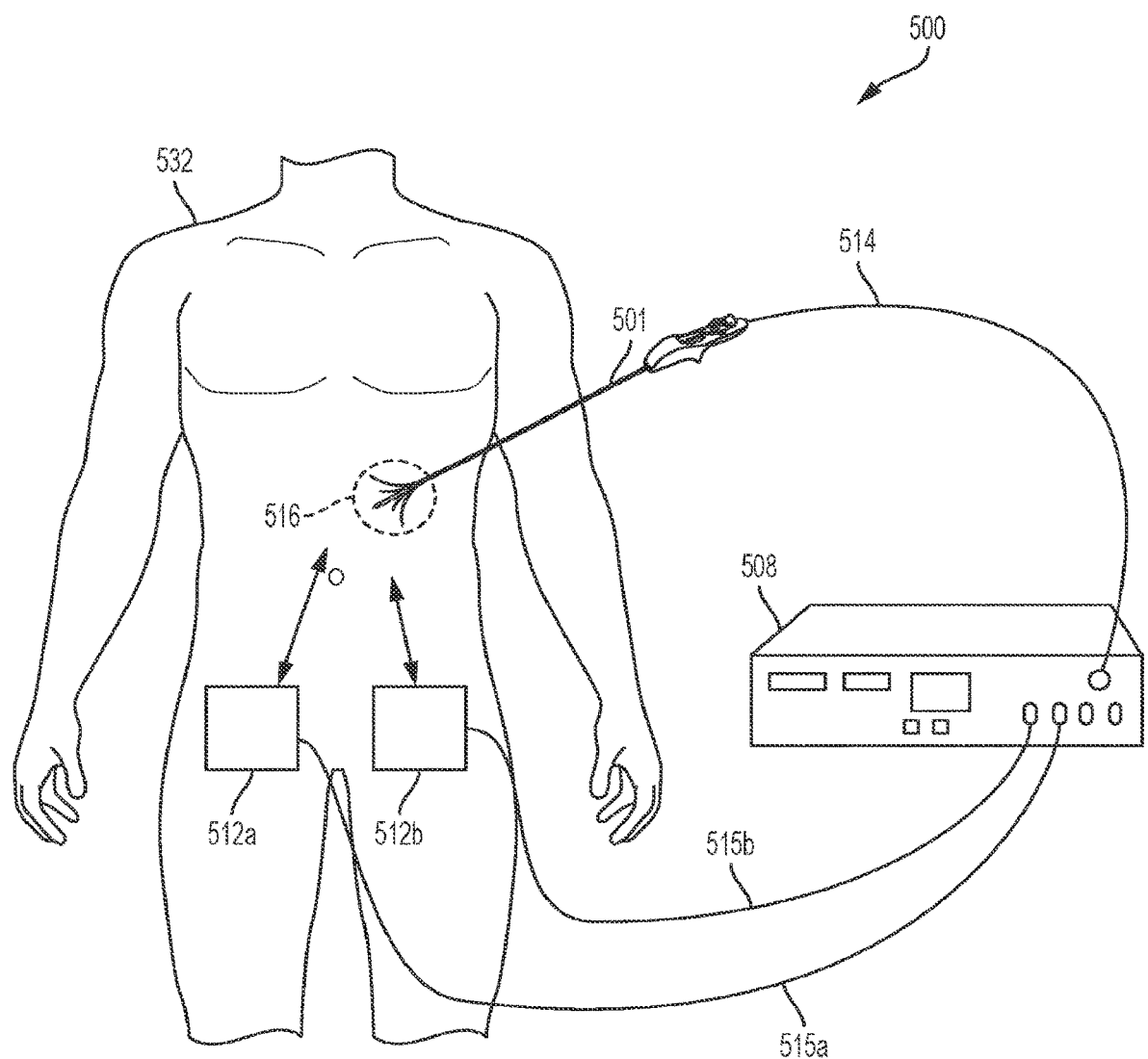
FIG. 10 illustrates a plan view of an embodiment of an HFIRE system including a single-pole tine-style electrode probe inserted into a target tissue of a patient and two external surface electrodes placed on the surface of a patient's body.

Referring now to FIG. 10, an embodiment using multiple external surface electrodes is illustrated. Skin surface electrodes 5l2a and 512b may be connected to HFIRE generator 508 via single pole cables 515a and 515b, respectively (other HFIRE protocols may be used, according to embodiments described herein). In an embodiment, skin surface electrodes 512a and 512b may be placed on skin surface 532 in different configurations to achieve desired HFIRE procedure results. Depending on the circumstances, surface electrodes 512a and 312b may be relatively large, relatively small, of average size, placed far apart, placed close together, or placed on skin surface 532 in a configuration that directs electrical energy away from certain internal organs or tissue and/or towards target region 516. While only two skin surface electrodes 512a and 512b are ill-suited, it can be appreciated that more skin surface electrodes may be used in some embodiments. Utilizing multiple surface electrodes provides for a wider electrical field dispersion through the tissue thus reducing thermal build-up when compared with a single surface electrode. Positioning multiple surface electrodes may also be advantageous in minimizing or eliminating muscle contractions by placing them such that the electrical current does not pass through areas of the body containing large muscle mass.

A methodology for performing HFIRE treatment using a single-pole electrode probe with corresponding external surface electrode will now be described with reference to FIG. 12. FIG. 12 illustrates a logic flow 1700 according to an embodiment. The logic flow 1700 may be representative of some or all of the operations executed by one or more embodiments described herein, such as HFIRE system 100, for example.

At 1702, a single-pole electrode probe may be inserted into a treatment region of a patient's body. The single-pole electrode probe may correspond to any of the embodiments described herein, and in some cases, may include an array of two or more single-pole electrode probes. In exemplary embodiments, the single-pole electrode probe may include one or more tines, which may be retractable.

FIG. 12 illustrates an embodiment of an exemplary HFIRE system 1800 suitable for implementing various embodiments as previously described. The embodiments are not limited in this context. System 1800 includes various common computing elements, such as one or more processors, which may be multi-core processors, co-processors, memory units, chipsets, controllers, peripherals, interfaces, oscillators, timing devices, video cards, audio cards, multimedia input/output (I/O) components, power supplies, and so forth.

As shown in FIG. 12, system 1800 comprises a controller 1802 including processing unit 1803, a system memory 1805 and I/O 1811. Memory 1805 may include or be connected to data storage 1807 and program storage 1809. Data storage 1807 may be used to store information collected by one or more sensors during an HFIRE procedure, for example. Program storage 1809 may include one or more HFIRE protocols and/or instructions for displaying a user interface on display 1804. The processing unit 1803 can be any of various commercially available processors, including without limitation an AMD® Athlon®, Duron® and Opteron® processors; ARM® application, embedded and secure processors, IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 180.

I/O 1811 provides an interface for system components including, but not limited to, controller 1802, display 1804, input device 1806, generator 1808, power distribution unit 1810, and imaging device 1814. I/O 1811 can be any of several types of bus structure that may further interconnect to a memory bus (with or without a memory controller), a peripheral bus, and a local bus using any of a variety of commercially available bus architectures. Interface adapters may connect to I/O 1811 via a slot architecture. Example slot architectures may include without limitation. Accelerated Graphics Port (AGP), Card Bus, (Extended) Industry Standard Architecture ((E)ISA), Micro Channel Architecture (MCA), NuBus, Peripheral Component Interconnect (Extended) (PCI(X)). PCI Express, Personal Computer Memory Card International Association (PCMCIA), and the like.

System 1800 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

Memory 1805, data storage 1807, and program storage 1809 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. Memory 1805, data storage 1807, and program storage 1800 can include non-volatile memory and/or volatile memory.

System 1800 may include various types of computer-readable storage media in the form of one or more lower speed memory units, including an internal (or external) hard disk drive (HDD), a magnetic floppy disk drive (FDD) to read from or write to a removable magnetic disk, and an optical disk drive to read from or write to a removable optical disk (e.g., a CD-ROM, DVD, or Blu-ray).

The drives and associated computer-readable media provide volatile and/or nonvolatile storage of data, data structures, computer-executable instructions, and so forth. For example, a number of program modules can be stored in the drives and memory units such as data storage 1807 and program storage 1809, including one or more application programs, other program modules, and program data. In one embodiment, the one or more application programs, other program modules, and program data can include, for example, the various applications and/or components to implement the disclosed embodiments.

A user can enter commands and information into the system 1800 through one or more wire/wireless input devices 1806, for example, a keyboard and a pointing device, such as a mouse. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the controller 1802 through I/O 1811 and can be connected by interfaces such as a parallel port. IEEE 1394 serial port, a game port, a USB port, an IR interface, and so forth.

A display 1804 is also connected to controller 1802 via I/O 1811, which may include a video adaptor. The display 1804 may be internal or external to a computer In addition to the display 1804, a computer typically includes other peripheral output devices, such as speakers, printers, and so forth.

System 1800 may include an imaging device 1814, which may be an ultrasound device, MRI system, or another commonly known imaging device that is off the shelf, or otherwise already used in a hospital setting. Imaging device 1814 may be used to visualize a treatment area prior to, during, or after an HFIRE procedure according to the embodiments described herein. However, the system 1800 may be designed such that it can incorporate such an imaging device 1814 into the system 1800, or alternatively it can interface with the controller 1802, such that the information or feedback received from the imaging device 1814 may be used by the user of system 1800.

System 1800 may also include generator 1808, which may be configured to performed any of the HFIRE protocols described herein, and may be controlled by controller 1802. Generator 1808 may be connected to a power distribution unit 1810, which may be configured to deliver electrical energy pulses according to an HFIRE protocol to an electrode 1812. As described herein, electrode 1812 may be of various configurations and achieve the goals of the present disclosure.

Figure 13B:
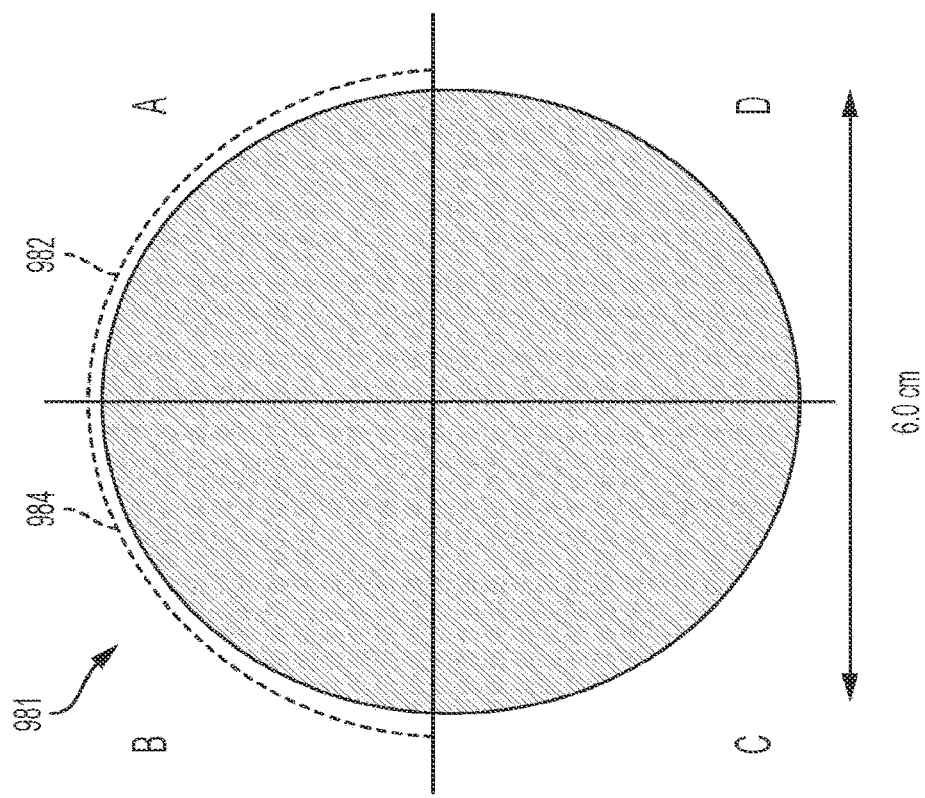
FIG. 13A-13D graphically depicts cumulative ablation volumes achieved using sequentially activated surface electrodes or surface electrodes positioned in different locations.
Figure 13A:
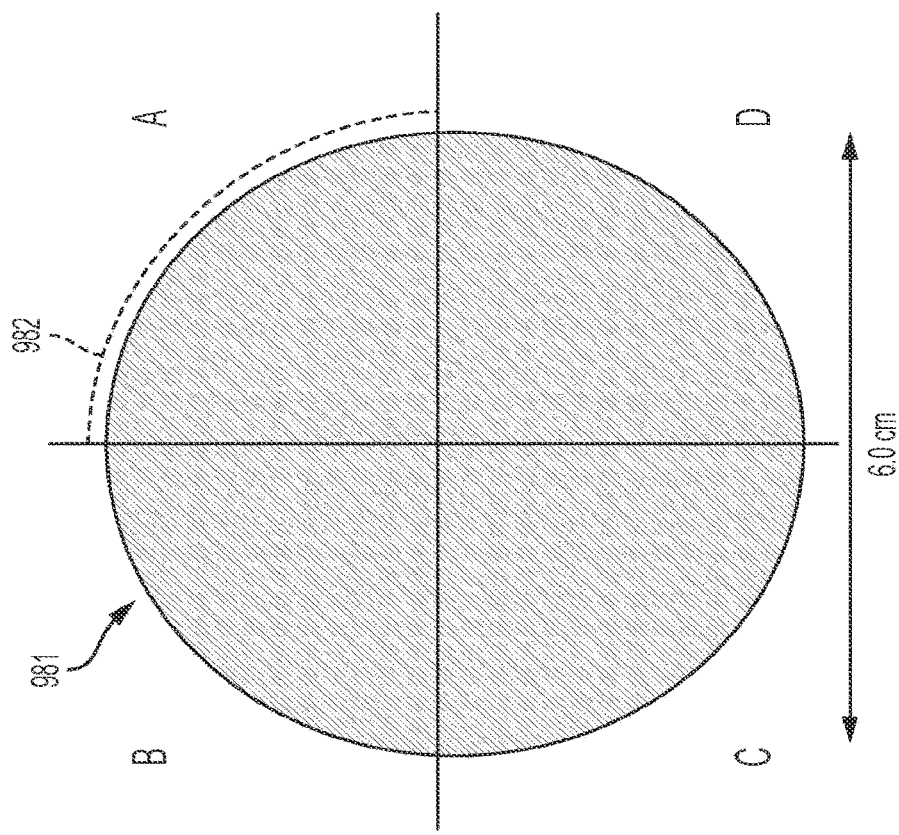
Figure 13D:
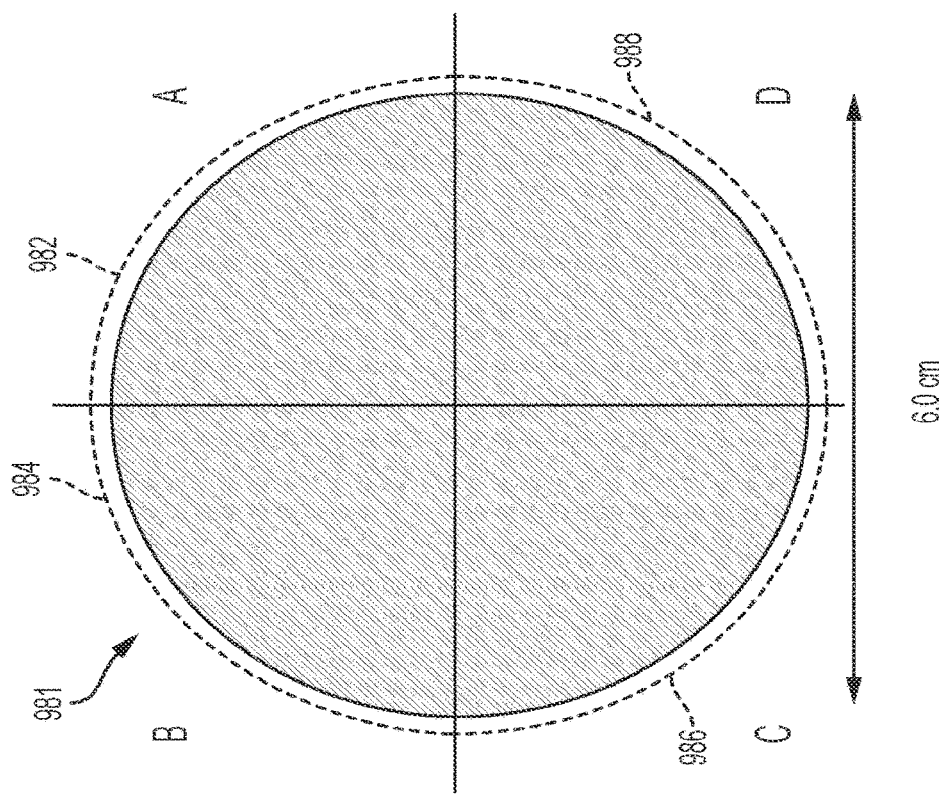
Figure 13C:
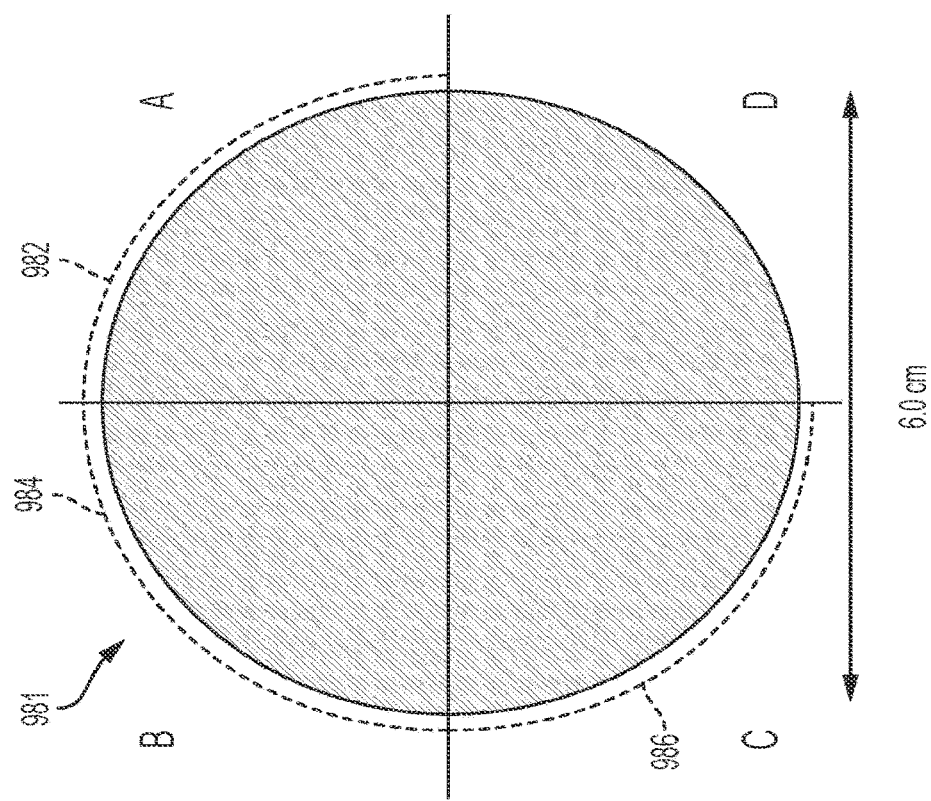

Referring now to FIG. 13A-FIG. 13D, a method of performing an HFIRE ablation procedure is illustrated. The method utilizes a surface electrode and a single pole, tined electrode probe, wherein the surface electrode is sequentially positioned in different locations on the patient's body to achieve a larger, more spherical ablation. FIG. 13A-13D depict a substantially spherical ablation zone 981, separated into four quadrants A-D for illustrative purposes. When the surface electrode is placed on the patient's body over quadrant A, the electrical field created between the inserted tined electrode probe and the surface electrode includes an "electrical pull" zone 982, which is formed in the tissue zone physically closest to the surface electrode (quadrant A). For a 6 cm ablation zone 980, the electrical pull zone 982 may increase the final ablation zone by up to 3 mm, depending on HFIRE parameters and tissue type of both the target zone and surrounding tissue. In the next step, the user places the surface electrode on the patient's body in the area of quadrant B, and then executes a second set of HFIRE electrical pulses. As shown in FIG. 13B, the resultant ablation zone includes a supplemental electrical pull zone 984. These steps are repeated for quadrants C and D, as shown in FIGS. 13C and 13D, thus creating additional electrical pull zones 986 and 988, each extending the ablation zone approximately 3 mm larger. Using the method described herein, a spherical ablation zone may be created which is up to 6 mm larger in diameter than an ablation zone created using only a single surface electrode. This approach may be advantageous in ensuring a more spherical ablation as the electrical circuit is completed over multiple spatial zones.

In yet another embodiment, the user may apply four or more spatially separated surface electrodes to the patient prior to the initiation of treatment. The HFIRE system may be programmed to automatically deliver a first set of pulses between internally placed probe and the first surface electrode, wherein a first electrical pull zone is created. The pulse algorithm may be programmed to then automatically switch the active surface electrode from the first to second surface electrode, followed by the delivery of HFIRE pulses, wherein a second electrical pull zone is created. These steps are repeated for the third and fourth surface electrodes. Advantageously, a more spherical, larger ablation is created, as compared to a single surface electrode protocol. Four surface electrodes in this example is not intended to be limiting, as it is within the conception of the invention to use additional surface electrodes or a single surface pad in the shape of a ring that may contain several surface electrodes that are independently activatable.

In yet another example, the method of using multiple surface electrodes may be completed as a supplemental procedure to ensure an adequate ablation margin has been created by the primary ablation procedure. The purpose of treating the margins surrounding the target zone is to ensure that all possible target cells have been successfully ablated or otherwise removed thereby lowering the risk for proliferation of the target cells. As previously described, the method of using multiple surface electrodes as a secondary procedure may result in up to a 10% increase in final ablation diameters (6 cm ablation with 6 mm secondary increase), further mitigating the risk of cancerous cell proliferation. In yet another embodiment, the method of using multiple surface electrodes may be applied as an adjunct to a surgical procedure. After a tissue mass, such as a cancerous breast tumor, has been surgically removed, the surface electrodes may be placed on the patient and the tined probe inserted into the cavity created by the removed tissue volume. Electrical pulses may then be applied as described above to ablate the cavity margins, thus ensuring that the margins are free of cancerous cells.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible.

What is claimed:

1. A method for ablating cells in a treatment site of a patient, the method comprising:
   advancing a monopolar electrode through a shaft positioned within the treatment site such that the monopolar electrode does not extend distally of a distal end of the shaft, wherein the distal end of the shaft is conductive;
   placing a surface electrode on a surface of the patient;
   activating a generator to apply a first set of electrical pulses between the conductive distal end of the shaft and the surface electrode in an amount sufficient to induce non-thermal ablation of the treatment site by high-frequency irreversible electroporation (HFIRE), wherein the first set of pulses include bi-phasic pulses having a delay between adjacent pulses and wherein the first set of electrical pulses have a voltage of between about 2,500 V and about 10,000 V, thereby enabling treatment while mitigating muscle contractions without the administration of a paralytic to the treatment site;
   wherein the first set of electrical pulses are configured to create a first ablation zone and a first electrical pull zone such that a size of the first ablation zone is increased in the first electrical pull zone,
   wherein the distal end of the shaft includes a sharp distal tip and the shaft includes an insulation sleeve portion that is positioned proximally of the sharp distal tip, and
   wherein the sharp distal tip comprises about 1 cm of exposure from the insulation sleeve portion.

2. The method of claim 1, wherein the treatment site includes an organ, and the shaft is positioned relative to the organ.

3. The method of claim 2, wherein the organ is a liver, kidney or lung.

4. The method of claim 2, wherein the monopolar electrode includes one or more deployable tines configured to deploy from the shaft proximal of the sharp distal tip, and wherein the method further comprises:
   deploying the deployable tines.

5. The method of claim 4, wherein the one or more deployable tines are arranged in multiple tiers around the shaft.

6. The method of claim 1, wherein the monopolar electrode does not extend through the sharp distal tip.

7. The method of claim 1, further comprising:
   moving the surface electrode to a second location on the surface of the patient; and
   activating the generator to apply a second set of electrical pulses between the conductive distal end of the shaft and the surface electrode while the surface electrode is in the second location.

8. The method of claim 7, wherein the second set of electrical pulses is configured to induce a second electrical pull zone.

9. The method of claim 1, wherein the first set of electrical pulses comprise a pulse width of between about 100 nanoseconds and about 10 microseconds;
   wherein the first set of electrical pulses delivered in burst widths of between about 500 nanoseconds and about 1 millisecond; and
   wherein a time delay between bursts is between about 1 millisecond and about 5 seconds.

10. A method for ablating cells in a treatment site of a patient, the method comprising:
   advancing a monopolar electrode through a shaft positioned within the treatment site, wherein the shaft includes a sharp distal tip that is electrically conductive and the monopolar electrode does not advance through the sharp distal tip;
   placing a surface electrode on a surface of the patient; and
   activating a generator to apply a first set of electrical pulses between the conductive distal tip of the shaft and the surface electrode in an amount sufficient to induce non-thermal ablation of the treatment site by high-frequency irreversible electroporation (HFIRE);
   wherein the first set of electrical pulses are configured to create a first ablation zone and a first electrical pull zone such that a size of the first ablation zone is increased in the first electrical pull zone; and wherein the first set of pulses are applied according to parameters that mitigate muscle contractions and obviate a need to deliver a paralytic, wherein the parameters comprise: a bi-phasic waveform, a pulse width of between about 100 nanoseconds and about 10 microseconds, a delay between adjacent pulses, a voltage of between about 2,500 V and about 10,000 V, burst widths of between about 500 nanoseconds and about 1 millisecond, and a time delay between bursts of between about 1 millisecond and about 5 seconds.

11. The method of claim 10, wherein the shaft includes an insulation sleeve portion that is proximal of the sharp distal tip.

12. The method of claim 11, wherein the sharp distal tip comprises about 1 cm of exposure from the insulation sleeve portion.

13. The method of claim 12, wherein the 1 cm of exposure of the sharp distal tip is an active distal tip.

14. The method of claim 10, wherein the monopolar electrode includes one or more deployable tines configured to deploy from the shaft proximally of the sharp distal tip, and wherein the method further comprises:
deploying the deployable tines.

15. The method of claim 14, wherein the one or more deployable tines are arranged in multiple tiers around the shaft.

16. The method of claim 15, further comprising:
moving the surface electrode to a second location on the surface of the patient; and
activating the generator to apply a second set of electrical pulses between the conductive distal tip of the shaft and the surface electrode while the surface electrode is in the second location.

17. The method of claim 16, wherein the second set of electrical pulses is configured to induce a second electrical pull zone.

18. The method of claim 17, wherein the second electrical pull zone increases the size of the initial ablation zone by up to 3 millimeters.

19. The method of claim 10, wherein the ablation zone comprises an ablation volume that is spherical in shape.

20. A method for ablating cells in a treatment site of a patient, the method comprising:
advancing a monopolar electrode through a shaft positioned within the treatment site, wherein the shaft includes a sharp distal tip that is electrically conductive and the shaft includes an insulation sleeve portion that is proximal of the sharp distal tip, wherein the sharp distal tip includes about 1 cm of exposure from the insulation sleeve portion, and wherein the monopolar electrode does not advance through the sharp distal tip;
placing a surface electrode on a surface of the patient; and
activating a generator to apply a first set of electrical pulses between the conductive distal tip of the shaft and the surface electrode in an amount sufficient to induce non-thermal ablation of the treatment site by high-frequency irreversible electroporation (HFIRE);
wherein the first set of electrical pulses are configured to create a first spherical ablation zone and a first electrical pull zone such that a size of the first spherical ablation zone is increased in the first electrical pull zone; and
wherein the first set of pulses are applied according to parameters that mitigate muscle contractions and obviate a need to deliver a paralytic, wherein the parameters comprise: a bi-phasic waveform, a pulse width of between about 100 nanoseconds and about 10 microseconds, a delay between adjacent pulses, a voltage of between about 2,500 V and about 10,000 V, burst widths of between about 500 nanoseconds and about 1 millisecond, and a time delay between bursts of between about 1 millisecond and about 5 seconds.

\* \* \* \* \*